United States Patent
Ozawa et al.

(10) Patent No.: US 7,324,674 B2
(45) Date of Patent: Jan. 29, 2008

(54) IMAGE PROCESSING DEVICE FOR FLUORESCENCE OBSERVATION

(75) Inventors: Takeshi Ozawa, Sagamihara (JP);
Katsuichi Imaizumi, Hachioji (JP);
Shunya Akimoto, Hachioji (JP);
Kazuhiro Gono, Sagamihara (JP)

(73) Assignee: Olympus Corporation, Tokyo (JP)

( * ) Notice: Subject to any disclaimer, the term of this patent is extended or adjusted under 35 U.S.C. 154(b) by 490 days.

(21) Appl. No.: 10/601,496

(22) Filed: Jun. 23, 2003

(65) Prior Publication Data
US 2004/0037454 A1 Feb. 26, 2004

(30) Foreign Application Priority Data
Jun. 26, 2002 (JP) .............................. 2002-186337

(51) Int. Cl.
*G06K 9/00* (2006.01)
(52) U.S. Cl. ..................................................... 382/128
(58) Field of Classification Search .................... None
See application file for complete search history.

(56) References Cited

U.S. PATENT DOCUMENTS

| | | | | |
|---|---|---|---|---|
| 4,125,828 A | * | 11/1978 | Resnick et al. ............. | 382/134 |
| 5,353,790 A | * | 10/1994 | Jacques et al. ............. | 600/315 |
| 5,647,368 A | * | 7/1997 | Zeng et al. ................. | 600/476 |
| 6,249,594 B1 | * | 6/2001 | Hibbard ....................... | 382/128 |

FOREIGN PATENT DOCUMENTS

| | | |
|---|---|---|
| EP | 1 256 310 A2 | 11/2002 |
| JP | 2000-270265 | 9/2000 |
| JP | 2001-137174 | 5/2001 |

OTHER PUBLICATIONS http://www.ledtronics.com/datasheets/Pages/chromaticity/097.htm.*

* cited by examiner

*Primary Examiner*—Matthew C. Bella
*Assistant Examiner*—Alex Liew
(74) *Attorney, Agent, or Firm*—Scully, Scott, Murphy & Presser, P.C.

(57) ABSTRACT

An image processing device having a very straightforward construction, for obtaining an image in which normal tissue and diseased tissue are easy to identify, comprises: an image synthesizing section that generates a synthesized image by synthesizing an image signal of reflected light image produced by illumination light obtained by illuminating body tissue with illumination light and an image signal of a fluorescent image obtained by illuminating the body tissue with excitation light; and a gain adjustment section that adjusts the gain of the image signal of the reflected light image and/or the image signal of the fluorescent image such that the boundary of the hues of the normal tissue and diseased tissue found from the optical characteristics of the respective tissues is contained in a predetermined range with respect to a prescribed standard chromaticity diagram, depending on whether the body tissue that is displayed on the synthesized image generated by the image synthesizing section is normal tissue or diseased tissue.

35 Claims, 12 Drawing Sheets

FIG.12A         FIG.12B
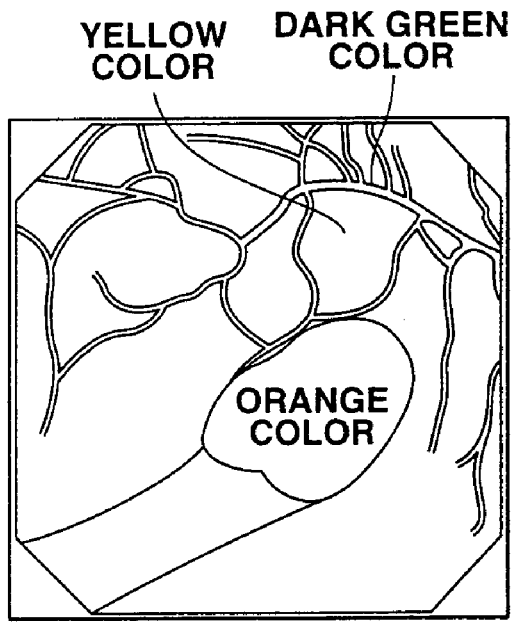 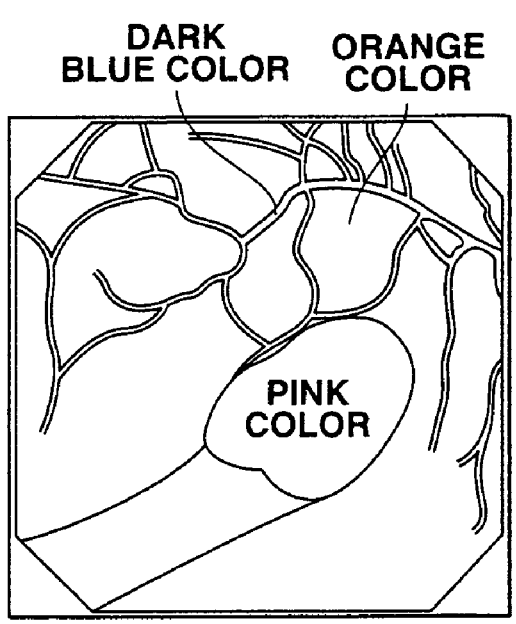
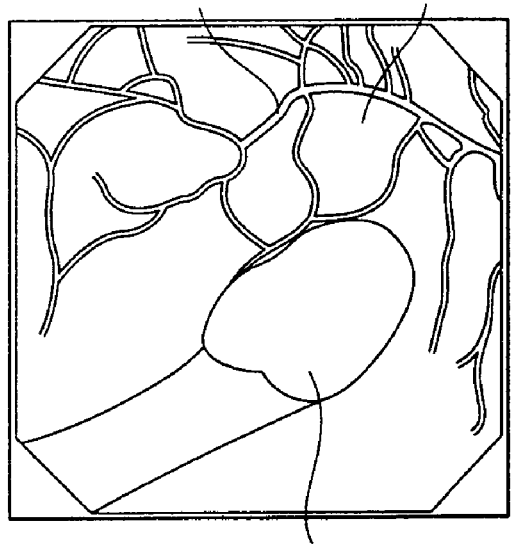 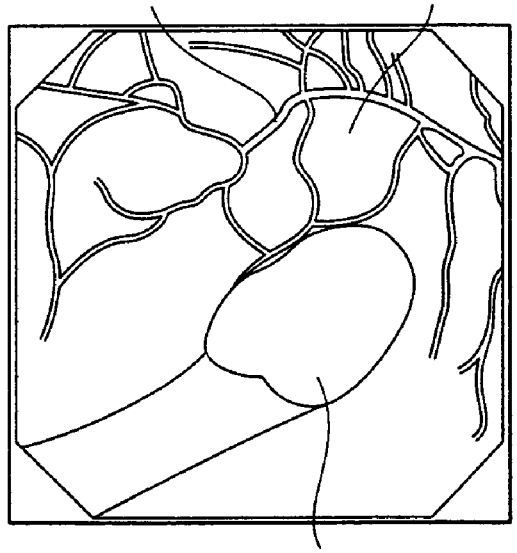
FIG.12C         FIG.12D

IMAGE PROCESSING DEVICE FOR FLUORESCENCE OBSERVATION

This application claims benefit of Japanese Application No. 2002-186337 filed in Japan on Jun. 26, 2002, the contents of which are incorporated by this reference.

BACKGROUND OF THE INVENTION

1. Field of the Invention

The present invention relates to an image processing device for fluorescence observation whereby a fluorescent image is obtained.

2. Description of the Related Art

In recent years, endoscope devices have come to be widely used in the field of medical treatment and the industrial field. In particular, in the field of medical treatment, endoscope devices are available whereby, in addition to obtaining a normal image using normal white light, an image is obtained whereby normal tissue and diseased tissue can easily be identified.

As an image processing device for fluorescence observation employed in such an endoscope device, as disclosed for example in Laid-open Japanese Patent Publication No. 2001-137174, an image processing device for fluorescence observation has been proposed whereby an image signal is generated in which, in essence, the relative intensity of fluorescence is converted to color and the intensity of reference light is converted to luminance.

As disclosed for example in Laid-open Japanese Patent Publication No. 2000-270265, an image processing device for fluorescence observation has also been proposed in which a synthesized image is constructed, wherein a fluorescent image and a background image are superimposed by allocating a single channel to the image signal of a fluorescent image and another channel to the image signal of a reflected light image, in an image signal used to form an image for fluorescence observation.

SUMMARY OF THE INVENTION

An image processing device for fluorescence observation according to the present invention comprises:

an image synthesizing section that generates a synthesized image by synthesizing an image signal of a reflected-light image produced by illumination light obtained by illuminating body tissue with illumination light and an image signal of a fluorescent image obtained by illuminating the body tissue with excitation light; and a gain adjustment section that adjusts the gain of the image signal of the reflected-light image and/or the image signal of the fluorescent image such that the boundary of the hues of the normal tissue and the diseased tissue found using the optical characteristics of the respective tissues is included in a predetermined range with respect to a prescribed standard chromaticity diagram, depending on whether the body tissue that is displayed in the synthesized image generated by the image synthesizing section is normal tissue or diseased tissue.

Also, an image processing device according to the present invention for fluorescence observation comprises:

a light source that emits illumination light of two different wavelength bands, namely, a wavelength band including the optical absorption band of hemoglobin and a wavelength band including the optical non-absorption band of hemoglobin and excitation light in a wavelength band for exciting fluorescence;

an image pickup section that picks up respectively two reflected light images produced by the reflected-light obtained by reflection after illuminating body tissue with illumination light of the two different wavelength bands from the light source and a fluorescent image produced by fluorescence excited by illuminating the body tissue with the excitation light from the light source; and an image processing section that generates a processed image by performing signal processing for the image signals of the two reflected-light images obtained through image pickup by the image pickup section and the image signal of the fluorescent image;

wherein the image processing section comprises:

a signal input section that inputs three image signals, namely, the image signals of the two reflected-light images picked up by the image pickup section and the image signal of the fluorescent image;

an image synthesizing section that generates a synthesized image by performing image synthesis for the image signal of the wavelength band including the optical absorption band of hemoglobin, the image signal of the wavelength band including the optical non-absorption band of hemoglobin and the fluorescent image signal; and a gain adjustment section that adjusts the gain of the three image signals that are input by the signal input section such that the boundary of the hues of the normal tissue and diseased tissue represented in the synthesized image synthesized by the image synthesis section is included in a range defined by the four points (0.21, 0.53), (0.18, 0.50), (0.23, 0.44) and (0.25, 0.49) with respect to the CIE 1976 UCS chromaticity diagram.

BRIEF DESCRIPTION OF THE DRAWINGS

FIG. 12A is a diagram showing an example of a synthesized image displayed with yellow-based colors, of examples of synthesized images displayed on a monitor when there is a boundary point outside a range defined by the four boundary points of FIG. 10;

FIG. 12B is a diagram showing an example of a synthesized image displayed with orange-based colors, of examples of synthesized images displayed on a monitor when there is a boundary point outside a range defined by the four boundary points of FIG. 10;

FIG. 12C is a diagram showing an example of a synthesized image displayed with green-based colors, of examples of synthesized images displayed on a monitor when there is a boundary point outside a range defined by the four boundary points of FIG. 10;

FIG. 12D is a diagram showing an example of a synthesized image displayed with blue-based colors, of examples of synthesized images displayed on a monitor when there is a boundary point outside a range defined by the four boundary points of FIG. 10;

DESCRIPTION OF THE PREFERRED EMBODIMENTS

Figure 1:
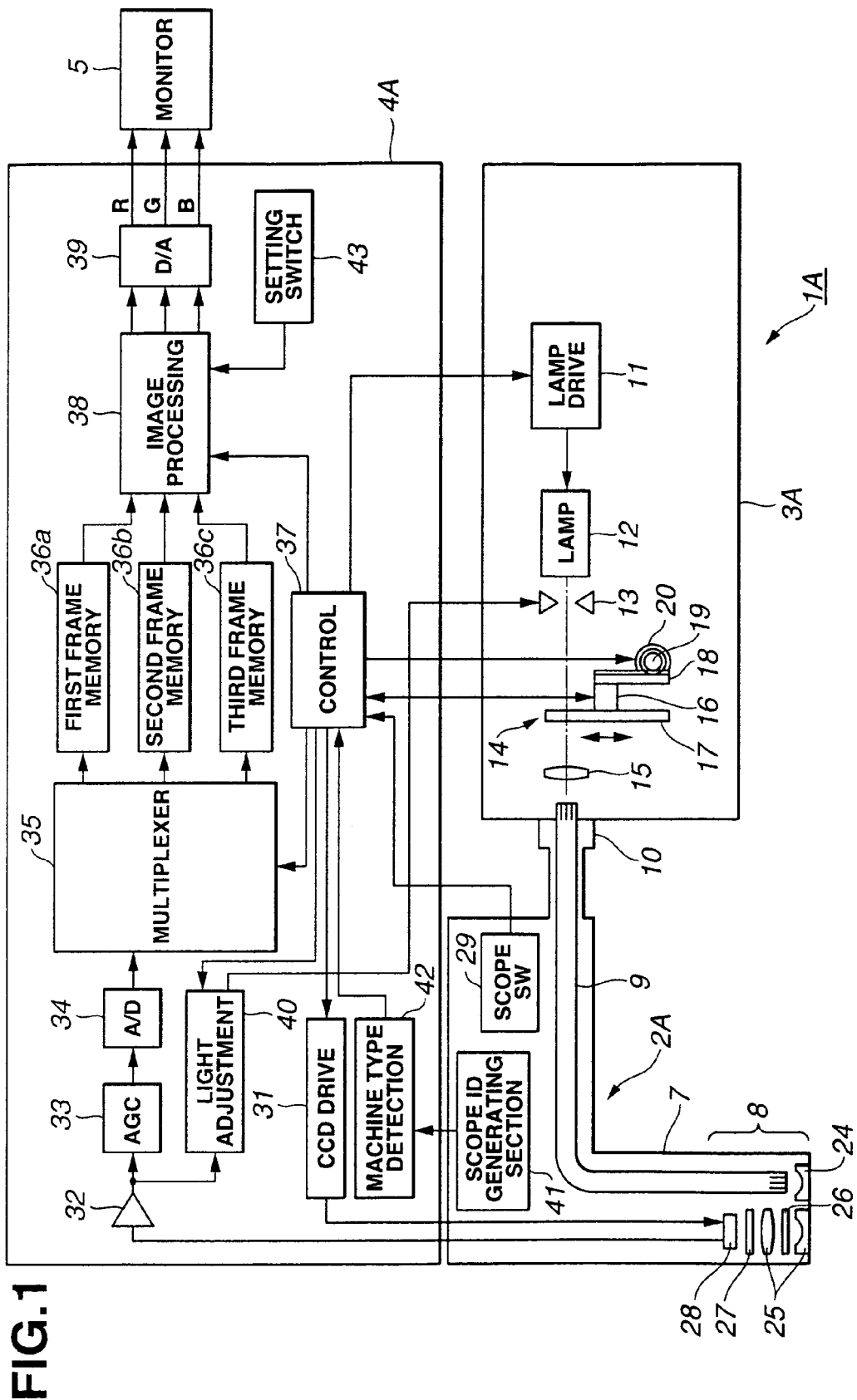
FIG. 1 is a block diagram showing the overall construction of an endoscope device comprising a first embodiment of the present invention.

An embodiment of the present invention is described below with reference to the drawings.

An endoscope device 1A comprising a first embodiment of the present invention shown in FIG. 1 comprises an electronic endoscope 2A for conducting observation by insertion into a body cavity, a light source device 3A that emits normal light for normal observation and excitation light, an image processing device for fluorescence observation (hereinbelow simply called an image processing device) 4A that performs signal processing for constructing a normal observation image and a fluorescent image and a monitor 5 capable of displaying a normal image produced by normal light and a fluorescent image produced by fluorescence.

The electronic endoscope 2A comprises an elongate insertion section 7 that is inserted into a body cavity. This insertion section 7 incorporates, in a distal end section 8, illumination means and image pickup means. Also, this insertion section 7 has inserted therein a lightguide fiber 9 for transmitting (guiding) normal light from normal observation and excitation light. A light source connector 10 provided at the proximal end on the base side of this lightguide fiber 9 is freely detachably connected with the light source device 3A.

The light source device 3A comprises a lamp 12 that emits light including from the infra-red wavelength band to the visible light band and that is driven to emit light by a lamp drive circuit 11, a light source diaphragm 13 that restricts the amount of light from the lamp 12 and is provided on an illumination optical path produced by this lamp 12, a changeover filter section 14 provided on the illumination optical path and a condensing lens 15 that collects the light passing through this changeover filter section 14.

This changeover filter section 14 comprises a changeover filter 17 whereby the filter that is arranged on the optical path is changed over by a displacement motor 20 and is rotated by means of a rotation motor 16, and a displacement motor 20 that displaces the changeover filter 17 together with the rotation motor 16 in a direction perpendicular to the optic axis, by driving in rotation a pinion 19 that meshes with a rack 18 mounted on the rotation motor 16.

Figure 2:
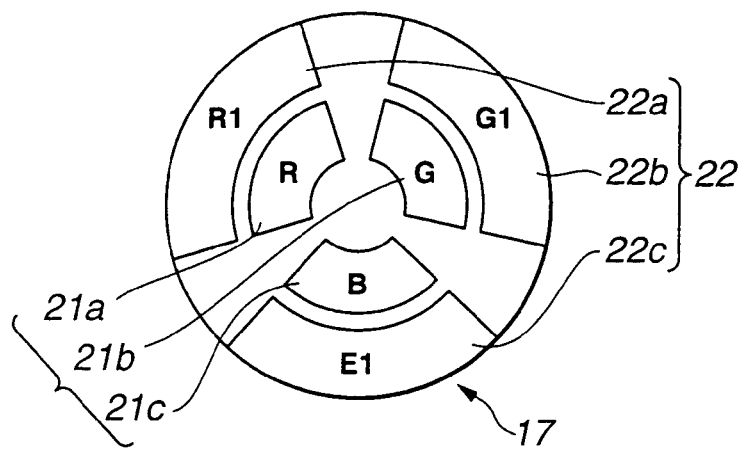
FIG. 2 is a view showing the construction of a changeover filter in which a filter for normal observation and a filter for fluorescence observation are provided.

The changeover filter 17 is provided with a normal observation RGB filter 21 and a fluorescence observation filter 22 concentrically with the inner circumference and outer circumference respectively, as shown in FIG. 2. The changeover filter 17 is arranged either to be set in an operating condition in the normal image mode (also called the "normal mode"), in which the normal illumination filter 21 is set on the optic path by driving the displacement motor 20, or to be capable of changing over to an operating condition in which the fluorescent image mode (also called the "fluorescent mode") is set by changing over from the normal illumination filter 21 to the fluorescent illumination filter 22.

The RGB filter 21 is arranged such as to be equally divided into three R, G and B filters 21a, 21b and 21c that respectively transmit light of the wavelength bands R (Red), G (Green) and B (Blue), in the circumferential direction. The respective R, G and B filters 21a, 21b and 21c are substantially continuously inserted successively in the optical path by rotating the RGB filter 21 by the rotation motor 16.

Figure 3A:
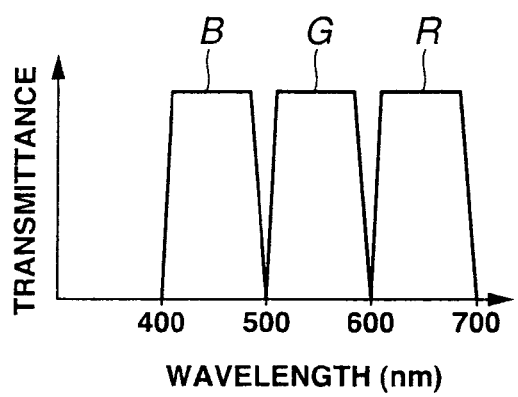
FIG. 3A is a graph showing the transmission characteristic with respect to wavelength of the filter for normal observation.

Also, the R, G and B filters 21a, 21b and 21c have filter characteristics that respectively transmit light of the wavelength bands 600 to 700 nm, 500 to 600 nm and 400 to 500 nm as shown by the transmission characteristics in FIG. 3A. In FIG. 3 and other Figures the filters are shown using the symbols R, G, B corresponding to their filter transmission characteristics, instead of using the symbols 21a, 21b, 21c (the same applies to the fluorescence observation filter 22, to be described).

Also, the fluorescence observation filter 22 is arranged to be equally divided into three R1, G1 and E1 filters 22a, 22b and 22c that respectively transmit narrow-band red (R1), narrow-band green (G1) and narrow-band excitation light (E1) in the circumferential direction. The respective R1, G1 and E1 filters 22a, 22b and 22c of the fluorescence observation filter 22 are successively inserted in the optical path by rotary drive of the rotation motor 16.

Figure 3B:
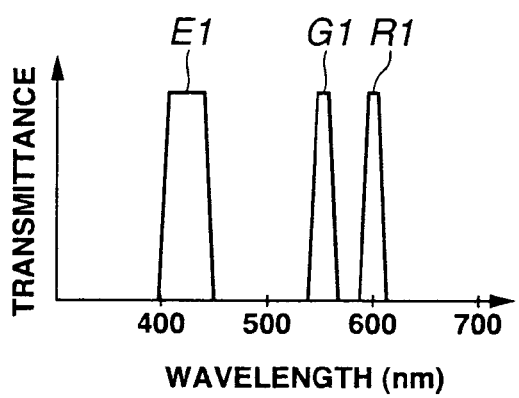
FIG. 3B is a graph showing the transmission characteristic with respect to wavelength of the filter for fluorescence observation.

Also, the R1, G1 and E1 filters 22a, 22b and 22c have filter characteristics that respectively transmit light of the wavelength bands 590 to 610 nm, 540 to 560 nm and 390 to 445 nm as shown by the transmission characteristics in FIG. 3B.

The illumination light from the light source device 3A is transmitted (guided) to the distal end of the insertion section 7 of the electronic endoscope 2A by a lightguide fiber 9. This lightguide fiber 9 transmits the fluorescence for fluorescence observation and the normal light for normal observation with little transmission loss. This lightguide fiber 9 is formed by for example a multi-component glass fiber or quartz fiber or other type of fiber.

The light that is transmitted to the distal end face of the lightguide fiber 9 passes through an illuminating lens 24 mounted at an illumination window facing the distal end face thereof and spreads out towards the site to be observed within the body cavity.

An observation window is provided in the distal end 8 adjacent to this illumination window. In the distal end 8, backward the observation window, there are arranged an subject lens system 25 for forming an optical image, a diaphragm 26 for spatially restricting the amount of incidence in order to achieve focusing from far to near, an excitation light cut-off filter 27 for cutting off the excitation light, and a charge-coupled element (abbreviated to CCD) 28 constituting an image pickup element that picks up images of the fluorescence and the reflected light, and performs for example monochromatic image pickup (or white/black image pickup).

As the image pickup element that picks up an image of the fluorescence and reflected light, instead of the CCD 28, it would be possible to employ a CMD (charge modulation device) image pickup element, a C-MOS image pickup element, an AMI (amplified MOS imager) or BCCD (back-illuminated CCD).

Figure 3C:
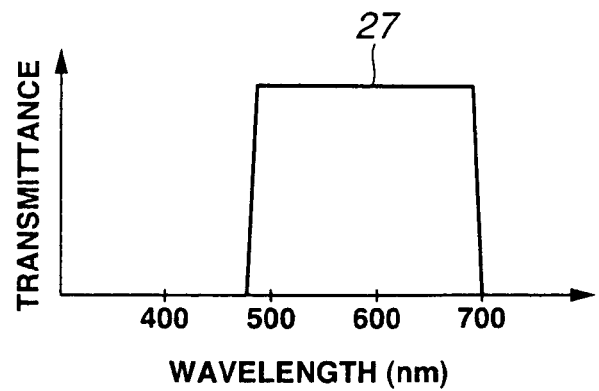
FIG. 3C is a graph showing the transmission characteristic with respect to wavelength of an excitation light cut-off filter.

The excitation light cut-off filter 27 is a filter for cutting off the excitation light that is used to generate fluorescence during fluorescence observation. The characteristic of this excitation light cut-off filter 27 is shown in FIG. 3C. As shown in FIG. 3C, this filter has a characteristic that transmits a wavelength band of 470 to 700 nm, i.e., that transmits visible light excluding wavelengths (400 to 470 nm) of part of the blue band.

This electronic endoscope 2A is provided with a scope switch 29 for performing a command operation for selecting fluorescent image mode and normal image mode and/or a command operation for freeze or release. The operating signal from this scope switch 29 is input to a control circuit 37. The control circuit 37 performs a control operation corresponding to this operating signal.

For example, the user may operate the normal mode switch of the mode changeover switches in the scope switch 29. When this is done, a condition is produced in which illumination light of the normal mode, i.e., R, G, B light is successively supplied to the lightguide fiber 9 by the light source device 3A by control of the control circuit 37. In addition, signal processing corresponding to the normal mode is performed by the image processing device 4A by controlling the control circuit 37.

Figure 4A:
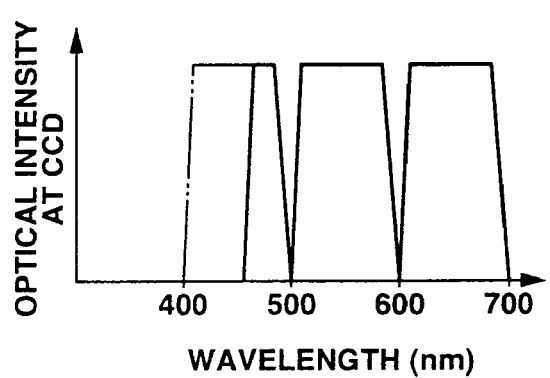
FIG. 4A is a graph showing the characteristic with respect to wavelength of the optical intensity detected photoelectrically by a CCD when a white subject is observed in normal observation mode.

FIG. 4A shows the optical intensity at the light-receiving surface (image pickup surface) of the CCD 28 when an image of a white subject such as white paper is picked up using normal mode.

In this case, illumination with R, G, B light is performed by the R, G and B filters 21a, 21b, 21c of characteristics shown in FIG. 3A. As shown in FIG. 3C, the filter characteristic of the excitation light cut-off filter 27 arranged in front of the CCD 28 is a characteristic that passes all of the G and R light but passes only some of the B light, on the long wavelength side thereof. Consequently, in the optical intensity at the light-receiving surface (image pickup surface) of CCD 28, the short wavelength side of B shown by the double-dotted chain line in FIG. 4A is cut off. The CCD 28 can therefore detect only some of the B light, on the long wavelength side, as shown by the solid line.

Consequently, in the period of illumination with B light by the B filter 21c, the amount of light detected photoelectrically by the CCD 28 drops from the level detected photoelectrically in the period of illumination with R light and G light by the other R and G filters 21a and 21b.

Consequently (in order to solve this), in normal observation mode, the control circuit 37 is arranged to obtain a normal image in which a "white balance" is achieved, either by increasing the amount of illumination light or by increasing the amplification factor in the image processing system when an image is picked up in the period of illumination using the B filter 21c, compared with when an image is picked up in the period of illumination using the R and G filters 21a and 21b.

Also, the user may operate the fluorescent mode switch of the mode changeover switch in the scope switch 29. When this is done, the light source device 3A assumes a condition in which illumination light of the fluorescent mode, i.e., R1, G1 and E1 light is successively supplied to the lightguide fiber 9 by controlling the control circuit 37. Furthermore, by controlling the control circuit 37, the image processing device 4A also assumes a condition in which signal processing is performed corresponding to the fluorescent mode.

FIG. 4A shows the optical intensity at the light-receiving surface (image pickup surface) of the CCD 28 when for example skin is observed using the fluorescent mode.

Figure 4B:
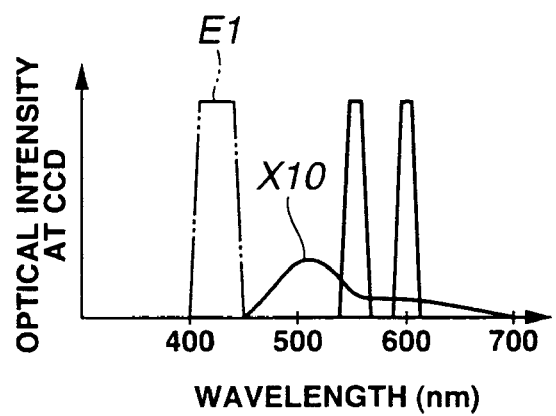
FIG. 4B is a graph showing the characteristic with respect to wavelength of the optical intensity detected photoelectrically by a CCD when skin is observed in fluorescence observation mode.

In this case, the skin is illuminated by the R1, G1 and E1 filters 22a, 22b and 22c shown in FIG. 3B. The reflected light produced by the R1, G1 filters 22a, 22b is within the pass-band of the excitation light cut-off filter 27 so that light corresponding to the reflection characteristic of the skin is detected photoelectrically by the CCD 28. However, as shown by the double-dotted chain line of FIG. 4B, the reflected light produced by the excitation light of the E1 filter 22c is outside the pass-band of the excitation light cut-off filter 27 and so is cut off. Also, that part of the fluorescence produced by the excitation light that is within the pass-band of the excitation light cut-off filter 27 is detected photoelectrically by the CCD 28. It should be noted that the amount of light of this fluorescence is considerably smaller than the amount of reflected light when illumination is performed using the R1 and G1 filters 22a and 22b, so the amount of light of this fluorescence is displayed in FIG. 4B multiplied for example by a factor of 10 (denoted by ×10).

The CCD 28 is driven by a CCD drive signal from a CCD drive circuit 31 provided within the image processing device 4A and the optical image on the CCD 28 is subjected to photoelectric conversion and the image signal obtained is output.

The amount of loss of this image signal during cable transmission is amplified by a preamplifier 32 representing signal input means provided within the image processing device 4A. The image signal is then further amplified to a prescribed level by an automatic gain control (AGC) circuit 33. The image signal is then converted from an analogue signal to a digital signal (image data) by an A/D conversion circuit 34. The converted image data passes through a multiplexer 35 that performs switching and is temporarily stored in a first frame memory 36a, second frame memory 36b and third frame memory 36c.

The CCD drive circuit 31 is controlled by a control circuit 37. Specifically, in the normal mode, as will be described, the amount of light detected photoelectrically by the CCD 28 when illumination is conducted using the B filter 21c is lower than in the case where illumination is conducted using the other R, G filters 21a and 21b, so that the control circuit 37 performs an electronic shutter function with respect to the CCD drive circuit 31.

Also, in the fluorescent mode, the amount of light detected photoelectrically by the CCD 28 in the period in which the fluorescent image is obtained by illumination with excitation light by the E1 filter 22c is much lower than in the case of the reflected light when illumination is conducted with the R1 and G1 filters 22a and 22b, so that the control circuit 37 likewise applies an electronic shutter function to the CCD drive circuit 31.

Also, the control circuit 37 controls the displacement motor 20 in accordance with the selected mode.

Also, the rotation motor 16 is controlled by the control circuit 37 and is arranged to output to the control circuit 37 the encoding signal of an encoder, not shown, mounted on for example the rotary shaft of the rotation motor 16. The control circuit 37 controls the CCD drive circuit 31 and/or changeover etc. of the multiplexer 35 in synchronization with the output of the encoder.

Also, the control circuit 37 controls changeover of the multiplexer 35 so that, in the normal mode, the image data picked up as a result of illumination using the R, G and B filters 21a, 21b and 21c is arranged to be successively stored in the first frame memory 36a, second frame memory 36b and third frame memory 36c, respectively.

Likewise, in the fluorescent mode, the control circuit 37 controls changeover of the multiplexer 35 such that the signals picked up as a result of the illumination using the R1, G1 and E1 filters 22a, 22b and 22c are respectively successively stored in the first frame memory 36a, second frame memory 36b and third frame memory 36c.

The image data stored in the frame memories 36a to 36c is input to an image processing circuit 38. The image processing circuit 38 then performs image processing that converts the input signals to output signals of a hue wherein normal tissue portions and diseased tissue portions can easily be identified. The image data is then converted to analogue RGB signals by a D/A conversion circuit 39 and output to the monitor 5.

In this embodiment, the image processing device 4A is arranged to input, in the fluorescent image mode, to the preamplifier 32 three image signals representing image input means, i.e., an image signal of a reflected light image obtained by picking up the light reflected by body tissues using the two narrow-band types of illumination light G1 and R1 and an image signal of the fluorescent image obtained by picking up the fluorescence generated from body tissue by the excitation light E1.

Also, in this embodiment, an image processing circuit 38 as synthesizing means is arranged to generate a synthesized single image for which, of the RGB channels, the image signal on the long wavelength side of the reflected light (wavelength band including the hemoglobin optical non-absorption band) is allocated to the B channel, the image signal of the fluorescent image is allocated to the G channel and the image signal on the short wavelength side of the reflected light (wavelength band including the hemoglobin optical absorption band) is allocated to the R channel. Furthermore, in this embodiment, the image processing circuit 38 is arranged to adjust the gains of the three image signals that are input, as will be described.

Also, in this image processing device 4A, there is provided a light adjustment circuit 40 that automatically controls the amount of the opening of the light source diaphragm 13 in the light source device 3A in response to the signal obtained through the preamplifier 32. This light adjustment circuit 40 is controlled by means of the control circuit 37.

Also, this control circuit 37 controls the lamp current of the lamp drive circuit 11 that drives light emission of the lamp 12. Also, this control circuit 37 performs control actions specified by manual operation of the scope switch 29.

Also, the electronic endoscope 2A comprises a scope ID generating section 41 that generates characteristic ID information including at least the machine type. When the electronic endoscope 2A is connected to the image processing device 4A, a machine type detection circuit 42 provided in the image processing device 4A detects the machine type information of the electronic endoscope 2A that is connected thereto and sends this machine type information to the control circuit 37.

The control circuit 37 outputs a control signal that sets parameters for matrix conversion and the like of the image processing circuit 38 to suitable values in accordance with the characteristics of the machine type of the electronic endoscope 2A that is connected thereto. The image processing circuit 38 also has connected thereto a setting switch 43 capable of selectively setting the parameters for matrix conversion and the like.

Also, the endoscope device 1A is capable of increasing the degree of separation of normal tissue and diseased tissue portions by setting, as shown in FIG. 3A to FIG. 3C, the filter characteristics: the RGB filter 21 and the filter 22 of the changeover filter 17, for fluorescence observation of the light source device 3A and the excitation light cut-off filter 27 provided on the image pickup optical path of the electronic endoscope 2A.

Figure 5A:
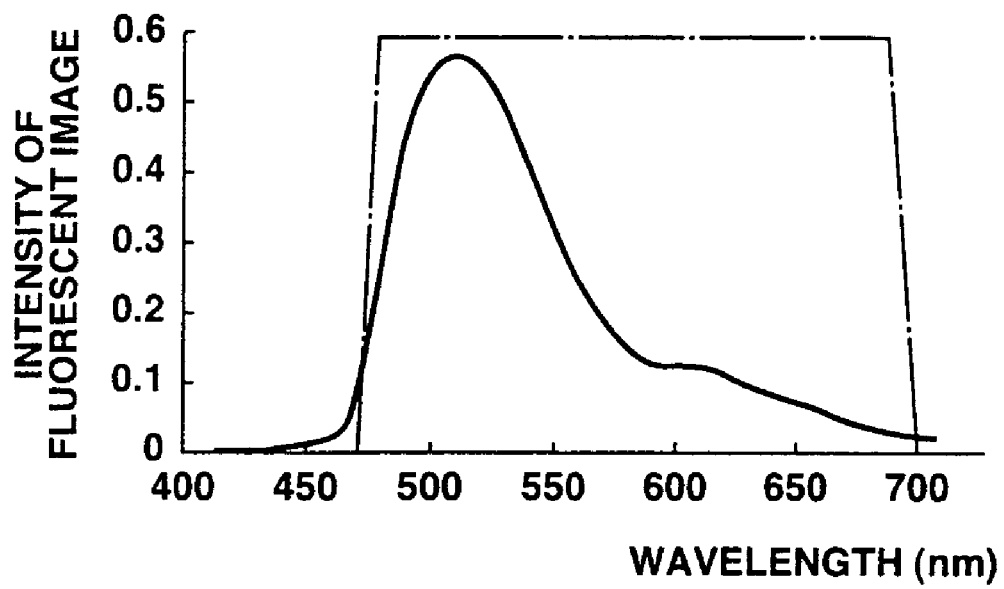
FIG. 5A is a graph showing an example of the characteristic with respect to body tissue of intensity distribution obtained from the wavelength of a fluorescent image.
Figure 5B:
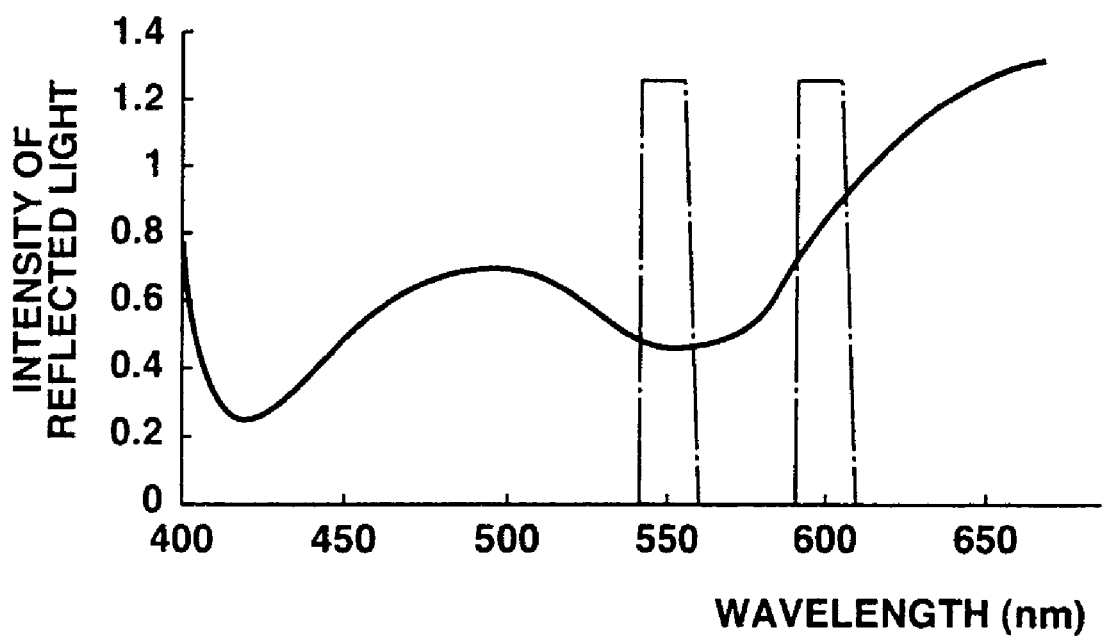
FIG. 5B is a graph showing an example of the characteristic with respect to body tissue of intensity distribution obtained from the wavelength of the reflected light.

FIG. 5A shows an example of the characteristic of the intensity distribution with respect to wavelength of the fluorescent image obtained from body tissues. FIG. 5B shows an example of the characteristic of the intensity distribution with respect to wavelength of reflected light obtained from body tissues.

As can be seen from FIG. 5A, the intensity characteristic of the fluorescent image shows a distribution characteristic having a peak in the vicinity of 520 nm. In this embodiment, the transmission characteristic produced by the excitation light cut-off filter 27 is set so as to include the wavelength band in the vicinity of this 520 nm.

Also, the wavelength characteristic of the reflected light of FIG. 5B shows large absorption due to hemoglobin in the vicinity of 550 nm and so shows a trough, in which the reflected intensity falls, in the vicinity of this wavelength. It should be noted that the vicinity of 600 nm is a non-absorption band of hemoglobin. The central wavelengths of the two filters 22a, 22b (G1 and R1 in the Figure) are set at 550 nm and 600 nm.

That is, in this embodiment, this band of the R1 filter 22a is set in a region where the degree of optical absorption of oxygenated hemoglobin is low and this band of the G1 filter 22b is set in a region where the degree of optical absorption of oxygenated hemoglobin is high.

The G1 and R1 light representing the first and second types of illumination light (reflected light) that are used for illumination in the fluorescent mode and image-pickup using the reflected light thereof have wavelength widths that are set for example to 20 nm (or they could be set to be less than 20 nm).

The transmittance of the light of the (long wavelength region of the) blue region that is cut off by the E1 filter 22c and of the (short wavelength region of the) blue region that is cut off by the excitation light cut-off filter 27 is set to be no more than OD4 (1/10,000).

In the wavelength region of the fluorescent image, its luminance level is relatively lower than that of the image produced by the reflected light, since the intensity of this fluorescent image is lower than the intensity of the image produced by the reflected light; identification using hue therefore also becomes difficult. The wavelength band of the fluorescent image is therefore set to a wide band including at least the wavelength of the peak (in the vicinity of 520 mm) of the fluorescence spectrum, in order to facilitate identification using hue by increasing the luminance level.

As described above, in this embodiment, the intensity of the fluorescent image is much weaker than that of the image obtained using reflected light, so, as shown in FIG. 5A, adopted is the excitation light cut-off filter 27 having a characteristic whereby a fluorescent image is obtained including the wavelength band in the vicinity of 520 nm, where peak intensity is obtained. In this way, a fluorescent image of good S/N can be obtained with the image processing device 4A of this embodiment.

Also, in this embodiment, the image processing device 4A is arranged to adjust the gains of three image signals by the image processing circuit 38 such that the boundary of the hues of normal tissue and diseased tissue is contained within the range defined by four points, as will be described, in the chromaticity diagram of the CIE (Commission Internationale d'Eclairage) 1976 UCS (Uniform-Chromaticity-Scale diagram), so that a hue (including luminance) is produced whereby normal tissue and diseased tissue are easily identified on the synthesized image in the fluorescent image mode.

Figure 6:
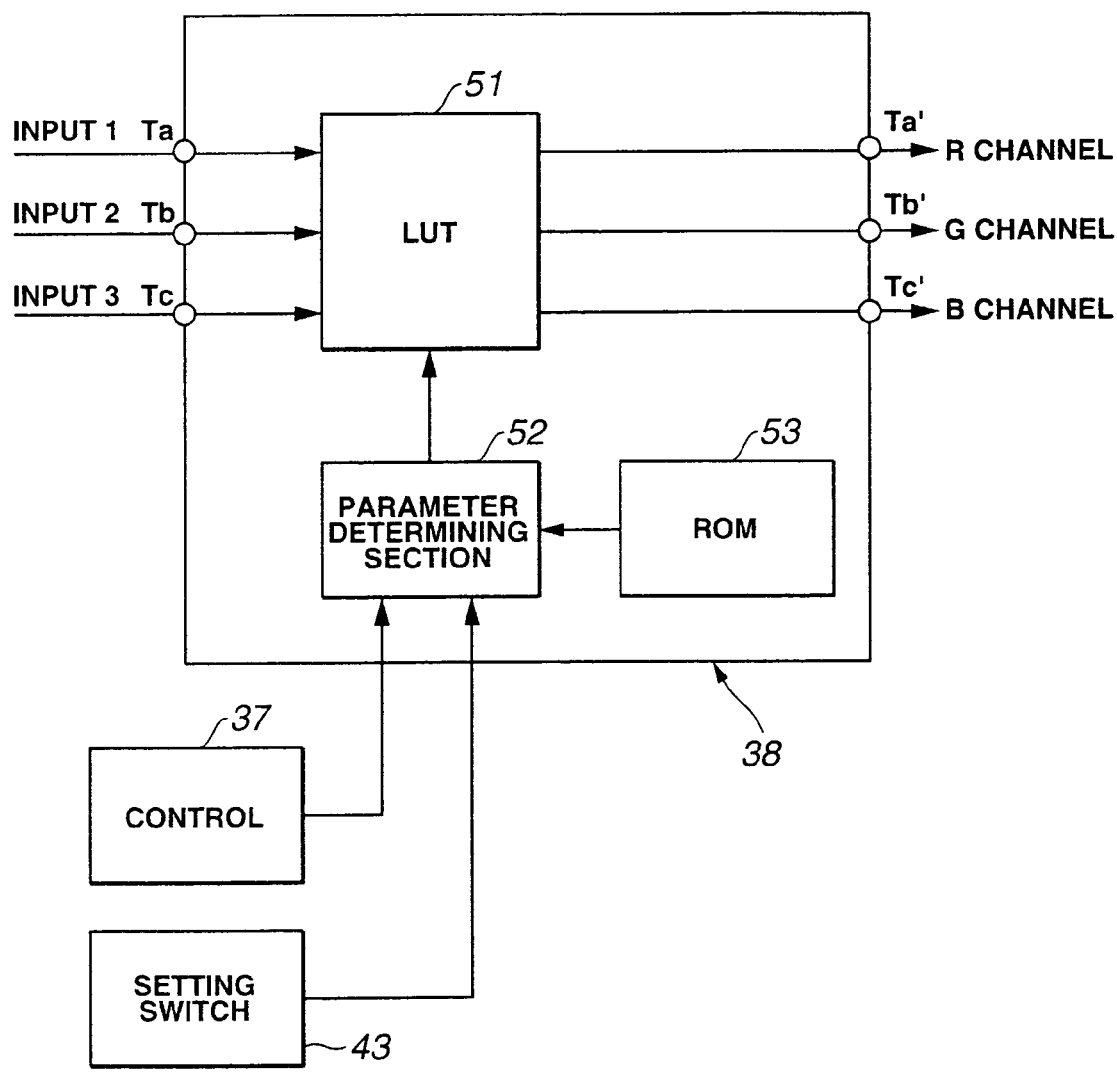
FIG. 6 is a block diagram showing the construction of the image processing circuit of FIG. 1.

As shown in FIG. 6, a look-up table (abbreviated to LUT in the Figure) 51 is adopted in the image processing circuit 38.

This look-up table 51 is connected with a ROM 53 through a parameter determining section 52. This parameter determining section 47 is connected with a control circuit 37 and setting switch 43.

A plurality of output values are stored beforehand in the ROM 53, and the output values determined with the aid of the parameter setting section 52 by the control signal from the control circuit 37 and the setting of the setting switch 43 are set in the look-up table 51.

In this embodiment, ROM 53 stores output values capable of adjusting the gains of three image points such that the boundary of the hues of the normal tissue and diseased tissue is included in a range defined by the four points (0.21, 0.53), (0.18, 0.50), (0.23, 0.44) and (0.25, 0.49) with respect to the CIE 1976 UCS chromaticity diagram.

The look-up table 51 is arranged such that the corresponding output values with respect to three signals input from input terminals Ta to Tc are read and output to the R, G and B channels from the output terminals Ta', Tb' and Tc'. In the normal mode, the look-up table 51 is set to have a characteristic whereby the input signals are directly output without modification.

The image data that is output to the R, G and B channels from the output terminals Ta', Tb' and Tc' is output to the monitor 5 after being converted to analogue RGB signals by a D/A conversion circuit 39 and is displayed as a synthesized image on this monitor 5.

The reason why the boundary of the hues of the normal tissue and diseased tissue is set so as to be included in a range defined by the four points (0.21, 0.53), (0.18, 0.50), (0.23, 0.44) and (0.25, 0.49) with respect to the CIE 1976 UCS chromaticity diagram as described above will now be described with reference to FIG. 7 to FIG. 12.

Figure 7:
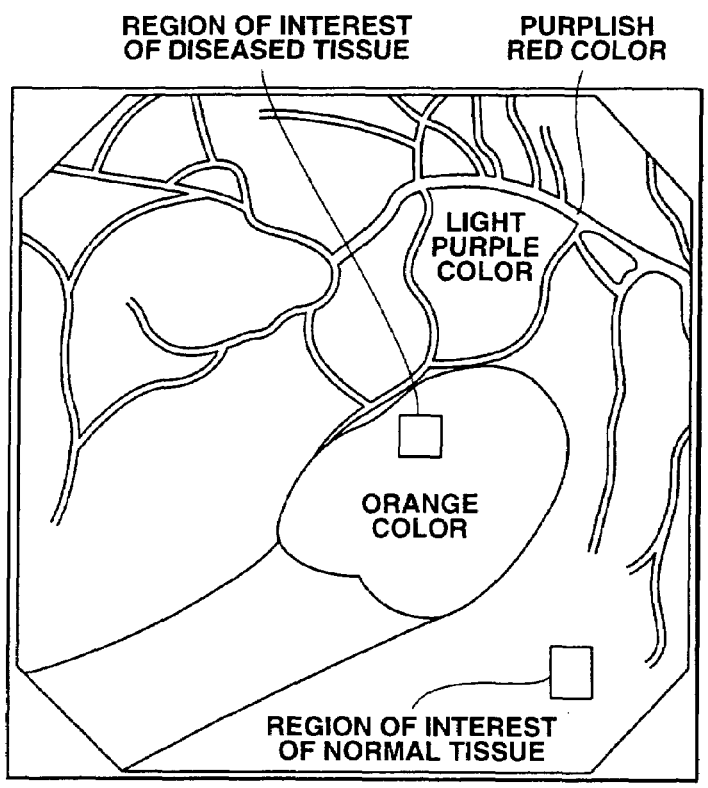
FIG. 7 is a diagram showing an example of image display when a region of interest is set in a synthesized image displayed on a monitor.

FIG. 7 is an example of an image display when the region of interest with respect to the synthesized image displayed on the monitor 5 is set. The color designations in FIG. 7 represent the color displayed in the vicinity thereof. The display is actually effected with the designated color. Hereinbelow, the synthesized image is represented as described above.

In this case, diseased tissue is present in the vicinity of the center of the image on the synthesized image and is displayed with an orange color in FIG. 7. The normal tissue surrounding this is displayed in purple. The blood vessels are displayed in a purplish red color and in some portions are difficult to differentiate from the normal tissue.

In this case, the region of interest is set by reference to the normal tissue and diseased tissue on the synthesized image and the average of the pixel values in this region is found. The average value that is found is the average hue in the region of interest. This is plotted on the CIE 1976 UCS chromaticity diagram.

Figure 8:
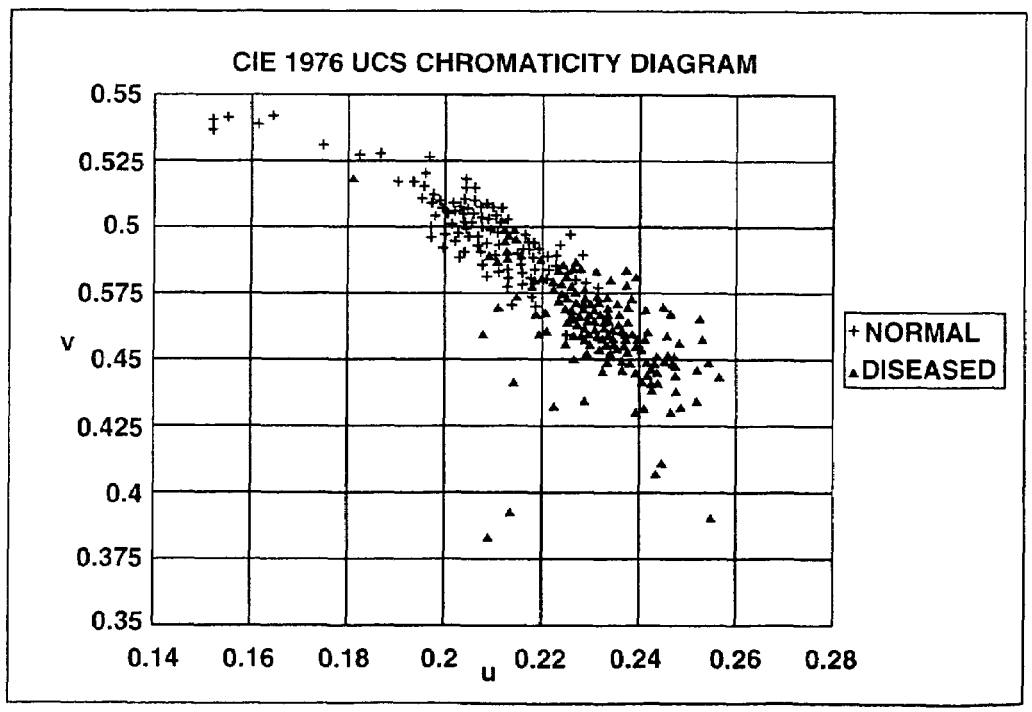
FIG. 8 is a chromaticity diagram in which the average values of pixels in regions of interest set in relation to normal tissue and diseased tissue on a synthesized image are plotted.

In this operation, a region of interest is specified taking for example a total of 288 data points by setting respectively two locations for each of the normal tissue and diseased tissue, with respect to 144 diseased sites in the lower digestive tract and these data are plotted on the chromaticity diagram. FIG. 8 shows a chromaticity diagram on which such data are plotted.

In the chromaticity diagram shown in FIG. 8, diseased tissue is distributed along the left diagonally upward direction from the vicinity of U 0.22, V 0.575 and diseased tissue is distributed along the right diagonally downward direction from the vicinity of U 0.22, V 0.575.

Figure 9:
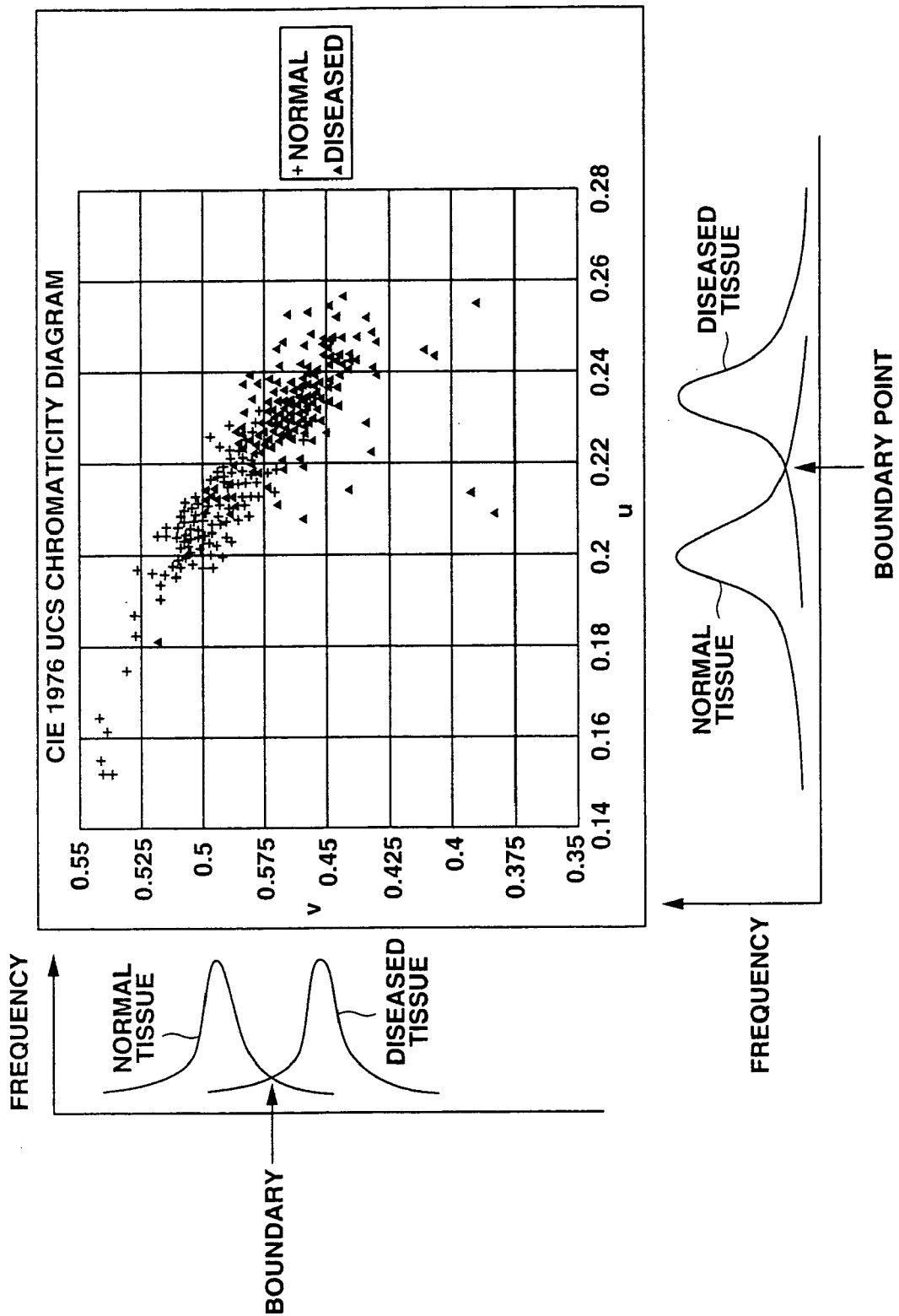
FIG. 9 is a view showing the probability distribution functions found respectively for the vertical axis V and horizontal axis U, assuming a normal distribution of aggregates of normal tissue and diseased tissue, with respect to the UCS chromaticity diagram of FIG. 8.

Assuming that the aggregates of the normal tissue and diseased tissue are normal distributions, the vertical axis V and horizontal axis U respective probability distribution functions are found as shown in FIG. 9. The points of intersection of the functions of the normal tissue and the diseased tissue are the boundary points of the respective aggregates.

This operation is performed with respect to the synthesized images synthesized by altering in various ways the gains of the three signals that are input to the image processing circuit 38 described above, i.e., the image signals of the reflected light images obtained by picking up the reflected light from the body tissues using the two types of narrow-band illumination light, G1 and R1, and the image signal of the fluorescent image obtained by picking up the fluorescence generated by body tissues by the excitation light E1 and the boundary points are plotted on the chromaticity diagram, wherein some points indicate that identification of normal tissue and diseased tissue is possible and some other points indicate that such identification is difficult in the synthesized image.

As described above, the image processing circuit 38 then generates a synthesized image in which the image signal of the long wavelength side (wavelength band including the optical non-absorption band of hemoglobin) of the reflected light is allocated to the B channel of the RGB channels, the image signal of the fluorescent image is allocated to the G channel of the RGB channels and the image signal of the short wavelength side (wavelength band including the optical absorption band of hemoglobin) of the reflected light is allocated to the R channel thereof.

Figure 10:
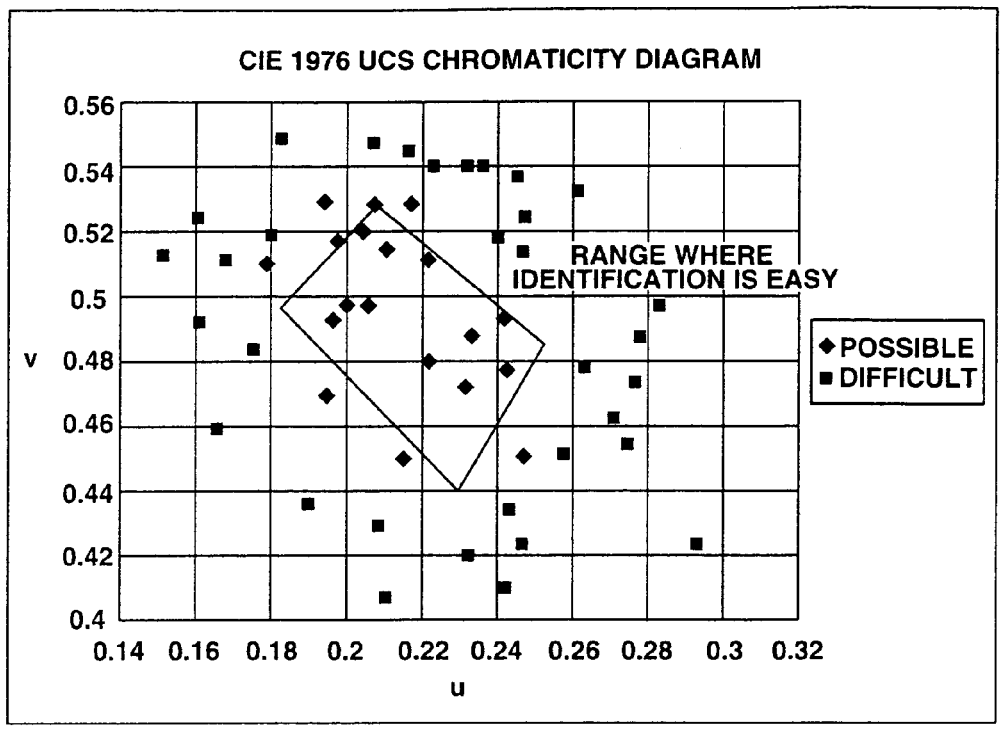
FIG. 10 is a chromaticity diagram in which boundary points are plotted, wherein some points indicate that it is possible to identify normal tissue and diseased tissue and some other points indicate that such identification is difficult, when the gains are varied.

FIG. 10 is a chromaticity diagram in which the boundary points are plotted, wherein some points indicate that identification of normal tissue and diseased tissue is possible and some other points indicate that such identification is difficult are plotted when the gains are changed.

As shown in FIG. 10, the boundary points of where identification of normal tissue and diseased tissue is possible are distributed in a range defined by four boundary points (0.21, 0.53), (0.18, 0.50), (0.23, 0.44) and (0.25, 0.49).

Setting the gains such that the boundary points lie within a range defined by these four boundary points (0.21, 0.53), (0.18, 0.50), (0.23, 0.44) and (0.25, 0.49) is therefore a prerequisite for being able to identify normal tissue and diseased tissue on the synthesized image.

Figure 11:
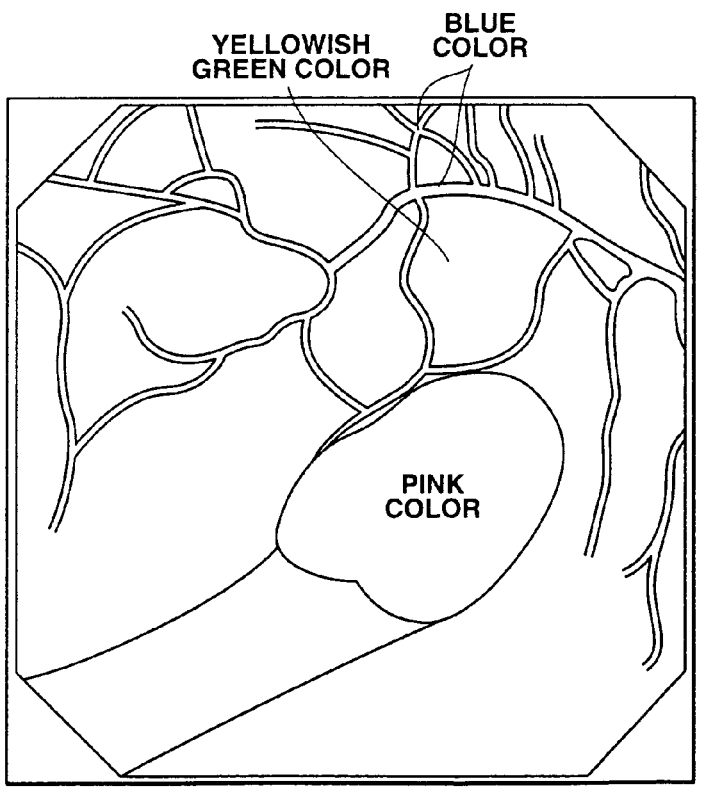
FIG. 11 is a diagram showing an example of a synthesized image displayed on a monitor when there is a boundary point at the center in a range defined by the four boundary points of FIG. 10.

For example, if the gains of the three signals that are input to the image processing circuit 38 are adjusted as described above such that there is a boundary point at the center of the range defined by the above four boundary points, a synthesized image as shown in FIG. 11 is displayed.

FIG. 11 is a synthesized image displayed on the monitor 5 in the case where there is a boundary point at the center of the range defined by the above four boundary points.

As shown in FIG. 11, in the synthesized image, the diseased tissue present in the vicinity of the center of the image is displayed with a pink color. The normal tissue around the diseased tissue is displayed with a yellowish green color. In this way, normal tissue and diseased tissue can easily be identified. The blood vessels are displayed with a blue color and so can easily be distinguished from the tissue.

In contrast, if for example synthesis is effected with the gains of the three signals input to the image processing circuit 38 as described above adjusted such that there are boundary points inside and outside the range defined by the above four boundary points, synthesized images as shown in FIGS. 12A to 12D are displayed.

In the synthesized images shown in FIGS. 12A to 12D, the normal tissue and diseased tissue are displayed with colors of the same color system, and so cannot easily be identified.

For example, in the synthesized image shown in FIG. 12A, diseased tissue is displayed with an orange color. Also, the normal tissue surrounding the diseased tissue is displayed with a yellow color. In this way, it is difficult to easily identify the normal tissue and the diseased tissue. The blood vessels are displayed in a dark green color, so distinguishing these from the tissues is difficult.

Likewise, in the synthesized images shown in FIGS. 12B to 12D, the normal tissue and diseased tissue cannot easily be identified. In the synthesized images shown in FIGS. 12B to 12D, the color labels represent the color that is displayed in the vicinity thereof.

The operation of this embodiment constructed as above is described below.

As shown in FIG. 1, the user connects the light source connector 10 of the electronic endoscope 2A to the light source device 3A and connects a signal connector, not shown, of the electronic endoscope 2A to the image processing device 4A. The user then sets the operating condition by connecting the power source of the respective devices by setting up the connected condition shown in FIG. 1. When this is done, the control circuit 37 performs the initial setting operation and controls to effect setting such that operation is performed in for example the normal mode in this initially set condition.

In this normal mode, the control circuit 37 controls the displacement motor 20 of the light source device 3A to set the changeover filter 17 in a position in which the RGB filter 21 at the inner periphery of the changeover filter 17 is in the illumination optical path.

The control circuit 37 then rotates the rotating motor 16. The R, G and B filters 21a, 21b and 21c of the changeover filter 17 are then successively arranged in the illumination optical path with the result that R, G and B illumination light obtained from the white light of the lamp 12 is then emitted towards the subject of observation.

In this normal mode, the R, G and B filters 21a, 21b and 21c for the illumination light (for the subject of observation) produced by the changeover filter are successively arranged in the illumination optical path.

The subject of image pickup is successively illuminated with R, G and B light and the reflected R, G and B light from the subject of image pickup is picked up by the CCD 28. The signal picked up by the CCD 28 is amplified and subjected to A/D conversion by the image processing device 4A before being successively stored in the first frame memory 36a, second frame memory 36b and third frame memory 36c by successive changeover of the multiplexer 35 using the control circuit 37.

The image data of the R, G and B color components stored in these frame memories 36a to 36c is simultaneously read with a prescribed frame period (for example 33 ms, i.e., 1/30 sec) and input to the image processing circuit 38.

In the normal mode, this image processing circuit 38 outputs the input signal as it is.

In this way, the image data of the R, G and B color components is passed through the D/A conversion circuit 39 to be converted to a standard analogue image signal, in this case, an RGB signal, and is output to the monitor 5 from the R, G and B channels. A normal observation image is displayed in color on the display screen of the monitor 5 (if illumination is effected with white light, reflecting the hue when the subject of image pickup is directly observed).

As described above, the amount of light reflected by the subject of image pickup when illumination is conducted through the B filter 21c is detected photoelectrically by the CCD 28 after the short wavelength side thereof has been cut off by the excitation light cut-off filter 27, so the amount of light detected photoelectrically in the image of this B color constituent is smaller than the amount of light detected photoelectrically in the images of the other R and G color constituents. If no adjustment were made, the white balance would therefore be lost.

In order to prevent this, the control circuit 37 uses the CCD drive circuit 31 to increase the amplification factor of the CCD 28, for example, doubled, when image pickup is effected during the period of illumination with the B filter 21c.

Also, the control circuit 37 controls the lamp drive circuit 11 to increase the lamp current, for example the value of the normal lamp current, that is used to drive the lamp 12 in the period of illumination by the B filter 21c, so as to increase the amount of illumination light B.

Also, the control circuit 37 controls the CCD drive circuit 31 to perform the function of an electronic shutter of the CCD 28. That is, in the R and G illumination periods, the control circuit 37 arranges that image pickup is effected only in part of the illumination period, using the CCD drive circuit 31 to drive the CCD 28 such as to produce a short image pickup period; in contrast, in the B illumination period, the control circuit 37 is arranged to produce a long image pickup period, utilizing the entire B illumination period for image pickup.

In this way, a white-balanced normal image is displayed on the monitor 5. Regarding the setting of the image pickup period by the electronic shutter, a specific value of the image pickup period is stored beforehand in memory or the like, not shown, within the control circuit 37, so that, when the image of a white subject is picked up, this subject is displayed in white on the monitor 5 (or, the image pickup period defined by the electronic shutter may be set specifically by picking up the image of a white subject on initial setting after connecting the power source). Instead of the image pickup period of the electronic shutter, the control circuit 37 could be arranged to store in memory the value of the CCD amplification factor or the value of the lamp current. These values could be employed singly or in combination.

In this way, the endoscope device 1A can be used to observe a subject in normal mode.

On the other hand, when a user wishes to perform fluorescence observation of a subject, such as for example a diseased site that is the subject of concern, the user operates the fluorescent mode switch of the mode changeover switch of the scope switch 29.

On receipt of this operating signal, the control circuit 37 effects changeover to the fluorescent mode by driving the displacement motor 20 of the light source device 3A, thereby displacing the changeover filter 17 so that the fluorescence observation filter 22 is set in a condition arranged on the illumination optical path.

When fluorescent mode is thus set, the lightguide fiber 9 of the electronic endoscope 2A is put in a condition such that illumination light of the fluorescent mode, i.e., R1, G1, E1 light as shown in FIG. 3B is successively supplied.

The subject is thereby successively illuminated with R1, G1 and E1 light. When illuminated with R1 and G1 light, the electronic endoscope 2A performs the same operation as in the case of successive illumination with R and G light in the normal mode. That is, in this case, in the electronic endoscope 2A, R1 and G1 light reflected by the subject is detected photoelectrically by the CCD 28. Under these circumstances, the CCD 28 performs image pickup without being affected by the excitation light cut-off filter 27.

In contrast, when the electronic endoscope performs illumination using the excitation light E1, the reflected light of this excitation light E1 is practically entirely blocked by the excitation light cut-off filter 27 and the fluorescence from the subject in the pass-band of this excitation light cut-off filter 27 is then detected photoelectrically by the CCD 28.

The intensity of this fluorescence is much smaller than the intensity of the R1 and G1 light reflected by the subject. Consequently, a bright fluorescent image (that can easily be compared with the image of the R1 and G1 reflected light of subject) is arranged to be displayed by having the control circuit 37 of the image processing device 4A performing R and G illumination in the normal mode described above and performing B illumination and by having performing an operation similar to the signal processing in the foregoing case.

Specifically, when image pickup of the R1 and G1 reflected light from the subject is performed, the control circuit 37 is arranged, by using the electronic shutter, to store in the first frame memory 36a and second frame memory 36b the image data picked up, by the CCD 28, only during a partial period of the illumination period.

In contrast, when illumination is performed with the excitation light E1, when this fluorescent image is picked up, the control circuit 37 increased the amplification factor of the CCD 28 from for example a factor of 10 to a factor of about 100, and also increases the lamp current and increases the amount of illumination light of the excitation light. In this case, the control circuit 37 stores the fluorescent image data that has been picked up in the third frame memory 36c.

The control circuit 37 then simultaneously reads the image data of the first frame memory 36a to the third frame memory 36c in a single frame period and inputs this image data to the image processing circuit 38.

The image processing circuit 38 is constructed as shown in FIG. 6, so that, for the input signals R1, G1 and EX, the corresponding output values are read from the look-up table 51 and output to the R, G and B channels. The image processing circuit 38 generates a synthesized image for which, of the RGB channels, the image signal on the long wavelength side of the reflected light (wavelength band including the hemoglobin optical non-absorption band) is allocated to the B channel, the image signal of the fluorescent image is allocated to the G channel and the image signal on the short wavelength side of the reflected light (wavelength band including the hemoglobin optical absorption band) is allocated to the R channel.

Also, in this case, compensation for the type of electronic endoscope 2A and/or the characteristics of the subject of image pickup is effected on the output values of the image processing circuit 38 and also output signals R', G' and B' is effected, wherein the gains of the three image signals are adjusted such that the boundary of the hues of the normal tissue and diseased tissue is included in a range defined by the four points (0.21, 0.53), (0.18, 0.50), (0.23, 0.44) and (0.25, 0.49) with respect to the CIE 1976 UCS chromaticity diagram.

The image data that is output to the R, G and B channels and is then converted to an analogue RGB signal by a D/A conversion circuit 39 and this analogue signal is output to the monitor 5 and displayed in pseudo color as a synthesized image on this monitor 5.

As described with reference to FIG. 11, normal tissue and diseased tissue can then easily be identified in the synthesized image displayed on the monitor 5.

As a result, with the image processing device 4A of this embodiment, a synthesized image is obtained in which normal tissue and diseased tissue can easily be identified by adjusting the gains of the three image signals using the image processing circuit 38 such that the boundary of the hues of the normal tissue and diseased tissue is included in a range defined by the four points (0.21, 0.53), (0.18, 0.50), (0.23, 0.44) and (0.25, 0.49) with respect to the CIE 1976 UCS chromaticity diagram.

Consequently, with the image processing device 4A according to this embodiment, the benefit is obtained that an image can be obtained in which normal tissue and diseased tissue can very easily be identified by means of a straightforward construction.

Also, the image processing circuit 38 may be constituted so as to be synthesized as a single image for which an image signal of the short wavelength side (wavelength band including the optical absorption band of hemoglobin) of the reflected light is allocated to the B channel of the RGB channels, an image signal of a fluorescent image is allocated to the G channel thereof and an image signal of the long wavelength side (wavelength band including the optical non-absorption band of hemoglobin) of the reflected light is allocated to the R channel thereof.

Figure 13:
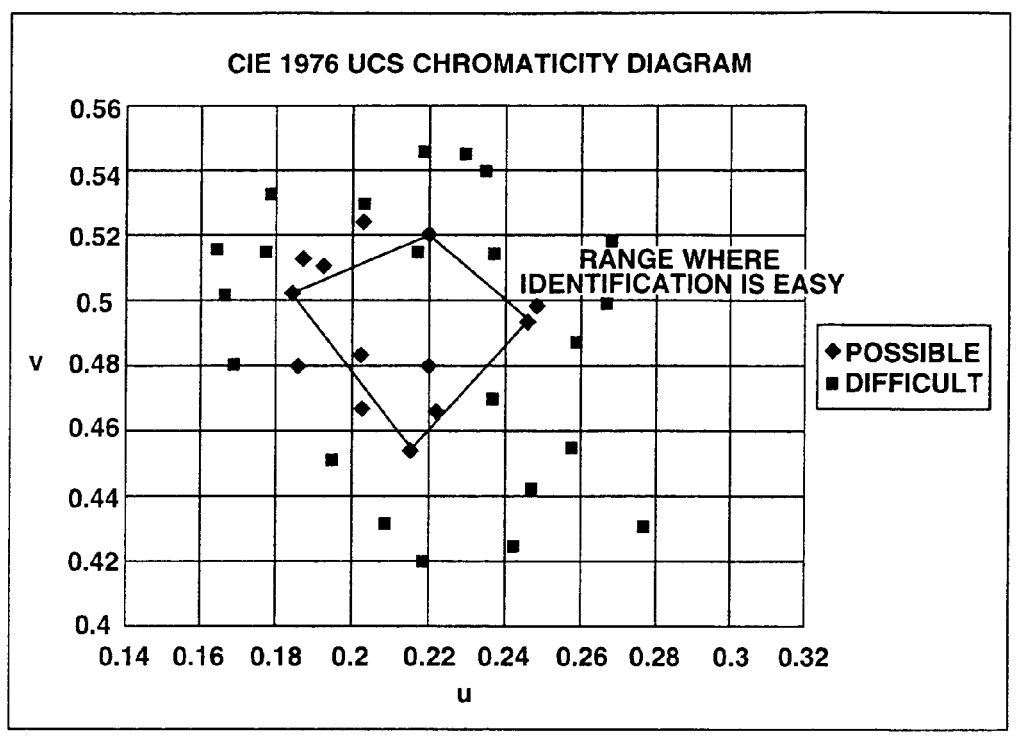
FIG. 13 is a chromaticity diagram showing a modified example in which boundary points are plotted, wherein some points indicate that it is possible to identify normal tissue and diseased tissue and some other points indicate that such identification is difficult, when the gains are varied.

In this case, the image processing circuit 38 is arranged to adjust the gains of the three input image signals such that the boundary of the hues of normal tissue and diseased tissue is included in a range defined by the four points (0.22, 0.52), (0.18, 0.50), (0.22, 0.45) and (0.25, 0.49) with respect to the CIE 1976 UCS chromaticity diagram as shown in FIG. 13.

FIG. 13 is a chromaticity diagram obtained in the same way as described with reference to the first embodiment in which the boundary points are plotted, wherein some points indicate that normal tissue and diseased tissue can be identified and some other points indicate that such identification is difficult, when the gains are varied.

As shown in FIG. 13, the boundary points where normal tissue and diseased tissue can easily be identified are distributed in a range defined by the four boundary points (0.22, 0.52), (0.18, 0.50), (0.22, 0.45) and (0.25, 0.49) with respect to the CIE 1976 UCS chromaticity diagram.

Thus, setting the gains such that the boundary points lie within a range defined by the four boundary points (0.22, 0.52), (0.18, 0.50), (0.22, 0.45) and (0.25, 0.49) with respect to the CIE 1976 UCS chromaticity diagram is the prerequisite for facilitating identification of normal tissue and diseased tissue on the synthesized image.

Figure 14:
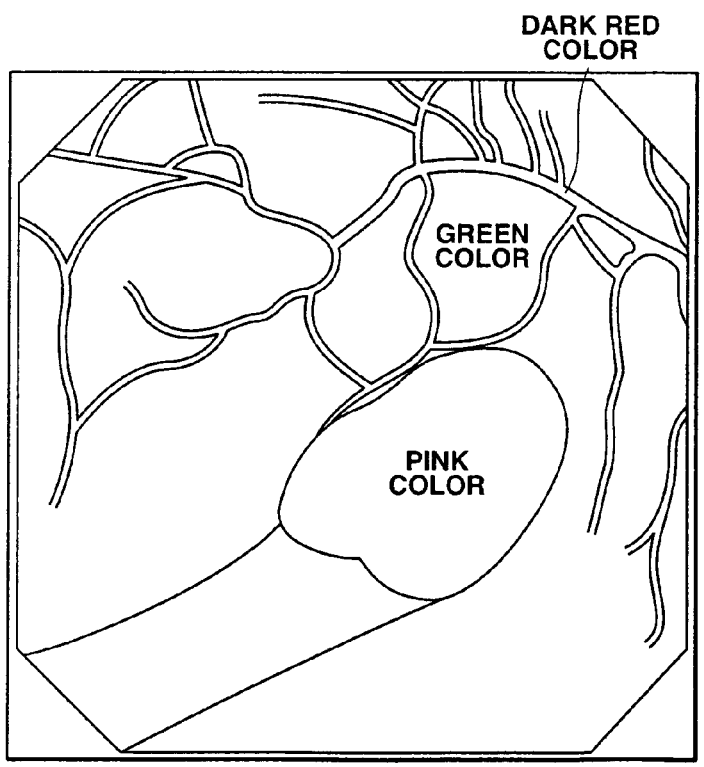
FIG. 14 is a diagram showing an example of a synthesized image displayed on a monitor when there is a boundary point at the center in a range defined by the four boundary points of FIG. 13.

Thus, for example, if the synthesis is conducted with the gains of the three signals that are input to the image processing circuit 38 as described above adjusted such that the boundary point is in the center of the range defined by the above four boundary points, a synthesized image as shown in FIG. 14 is displayed.

FIG. 14 is a synthesized image that is displayed on the monitor 5 when there is a boundary point at the center of the range defined by the above four boundary points.

As shown in FIG. 14, the synthesized image is displayed with the diseased tissue present in the vicinity of the center of the image shown in a pink color. The normal tissue surrounding the diseased tissue is shown in a green color. In this way, the normal tissue and diseased tissue can easily be identified. Also, the blood vessels can easily be distinguished from the tissue, since the blood vessels are displayed in a dark red color.

On the other hand, if for example synthesis is conducted with the gains of the three signals that are input to the image processing circuit 38 as described above adjusted such that there are boundary points inside and outside the range defined by the above four boundary points, synthesized images as shown in FIGS. 15A to 15D are displayed.

In the synthesized images shown in FIGS. 15A to 15D, normal tissue and diseased tissue are displayed with colors of the same system, so they are difficult to identify easily.

Figure 15A:
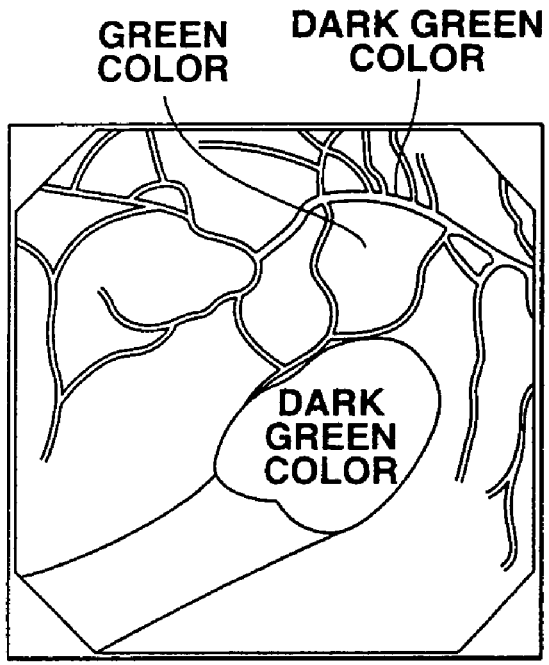
FIG. 15A is a diagram showing an example of a synthesized image displayed with green-based colors, of examples of synthesized images displayed on a monitor when there is a boundary point outside a range defined by the four boundary points of FIG. 13.

For example, in the case of the synthesized image shown in FIG. 15A, the diseased tissue is displayed in a dark green color and the normal tissue surrounding the diseased tissue is displayed in a green color. It is therefore difficult to identify easily the normal tissue and diseased tissue. The blood vessels are displayed in a dark green color and are difficult to distinguish from the tissue.

Figure 15B:
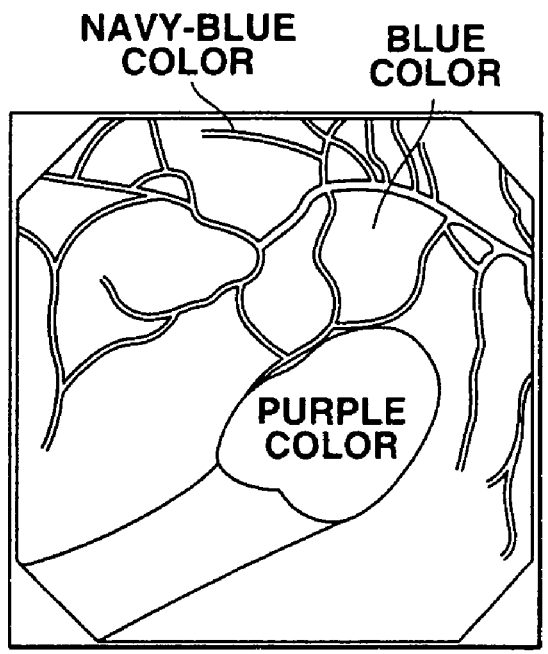
FIG. 15B is a diagram showing an example of a synthesized image displayed with purple-based colors, of examples of synthesized images displayed on a monitor when there is a boundary point outside a range defined by the four boundary points of FIG. 13.
Figure 15C:
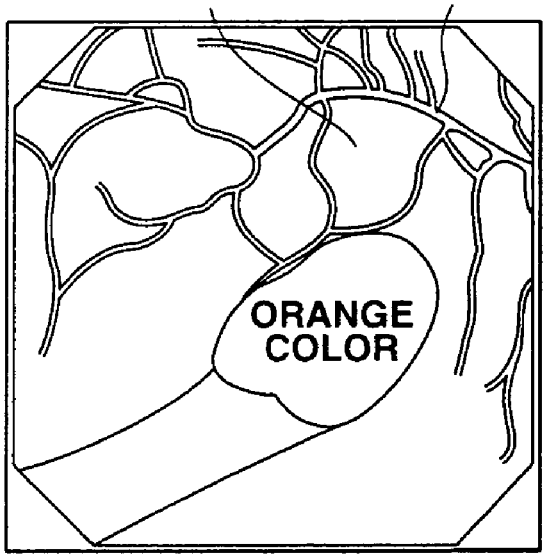
FIG. 15C is a diagram showing an example of a synthesized image displayed with a yellow-based color, of examples of synthesized images displayed on a monitor when there is a boundary point outside a range defined by the four boundary points of FIG. 13.
Figure 15D:
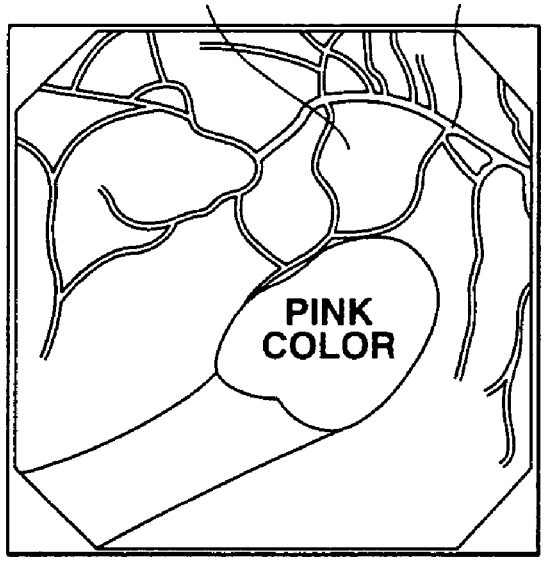
FIG. 15D is a diagram showing an example of a synthesized image displayed with orange-based colors, of examples of synthesized images displayed on a monitor when there is a boundary point outside a range defined by the four boundary points of FIG. 13.

Likewise, in the case of the synthesized images shown in FIGS. 15B to 15D, normal tissue and diseased tissue are difficult to identify easily. It should be noted that, in the synthesized images shown in FIGS. 15B to 15D, the color indicates the display color in the vicinity thereof.

With such a construction, the image processing circuit 38 generates a synthesized image by allocating the image signal of the short wavelength side (wavelength band including the optical absorption band of hemoglobin) of the reflected light to the B channel of the RGB channels, allocating the image signal of the fluorescent image to the G channel thereof allocating the image signal of the long wavelength side (wavelength band including the optical non-absorption band of hemoglobin) of the reflected light to the R channel thereof, and as a result, the gains of the three image signals are adjusted such that the boundary of the hues of the normal tissue and diseased tissue is included in a range defined by the four points (0.22, 0.52), (0.18, 0.50), (0.22, 0.45) and (0.25, 0.49) of the CIE 1976 UCS chromaticity diagram. The image data that is output to the R, G and B channels is converted into an analogue RGB signal by the D/A conversion circuit 39 before being output to the monitor 5 and is displayed with pseudo color as a synthesized image by this monitor 5.

In the synthesized image displayed on the monitor 5, as described with reference to FIG. 14, the normal tissue and diseased tissue can then easily be identified.

In this way, the same benefits as in the case of the first embodiment described above are obtained with the image processing device of this embodiment.

It should be noted that the endoscope device 1A could also be constituted with the light source device 4A, in addition to the changeover filter 17, being provided with a filter that cuts off excitation light in the vicinity of 400 nm, which is the excitation wavelength of porphyrin.

Figure 16A:
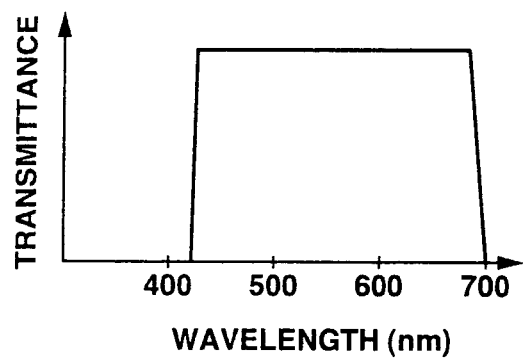
FIG. 16A is a graph showing the transmission characteristic with respect to wavelength of a filter that is provided to remove excitation light in the vicinity of 400 nm in addition to a changeover filter.

As shown in FIG. 16A, this filter has a characteristic that cuts off a shorter wavelength side of the blue color, different from the transmission characteristic of the E1 filter 22c (shown in FIG. 3B).

Figure 16B:
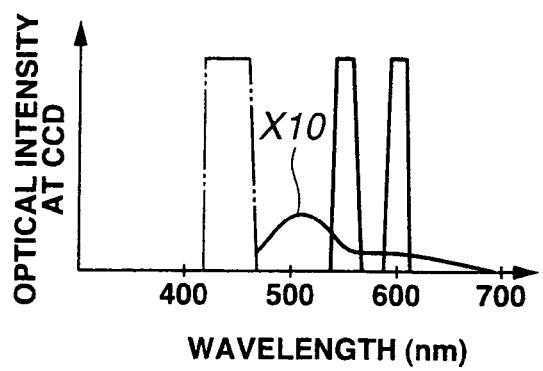
FIG. 16B is a graph showing the transmission characteristic with respect to wavelength of the optical intensity detected photoelectrically by a CCD when skin is observed in the fluorescence observation mode of a filter that is provided, in addition to a changeover filter, to remove excitation light in the vicinity of 400 nm.

Consequently, when the control circuit 37 performs selection such that this filter is arranged on the optical path, when skin is observed in the fluorescent mode, the characteristic of the CCD 28 is as shown in FIG. 16B. In this case, in the endoscope device 1A, more of the excitation light reaches deeper portions of the tissue, so the intensity of the fluorescence from the deeper portions is increased and the effect of self-fluorescence produced by porphyrin can be alleviated by cutting off excitation light in the vicinity of 400 nm, which is the excitation wavelength of porphyrin.

Also, the endoscope device 1A could be constituted with the electronic endoscope 2A provided with a filter that cuts off excitation light and porphyrin fluorescence, instead of the excitation light cut-off filter 27.

Figure 17A:
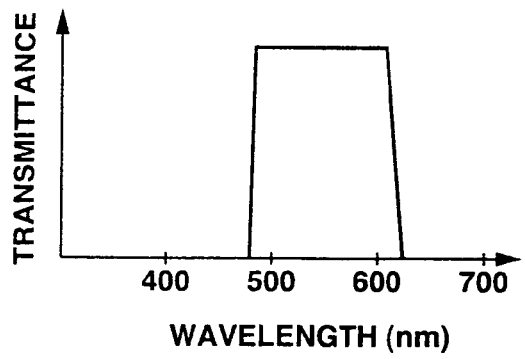
FIG. 17A is a graph showing the transmission characteristic with respect to wavelength of a filter that is provided, instead of an excitation light cut-off filter, to remove excitation light in the vicinity of 400 nm.

This filter is set so as to transmit 490 to 620 nm, as shown in FIG. 17A (and therefore not to transmit red light with a wavelength of more than 620 mm, or than 630 mm, a little longer than that). Thus, the endoscope device 1A is set so as to cut off the porphyrin fluorescence band, i.e., part of the red color.

Figure 17B:
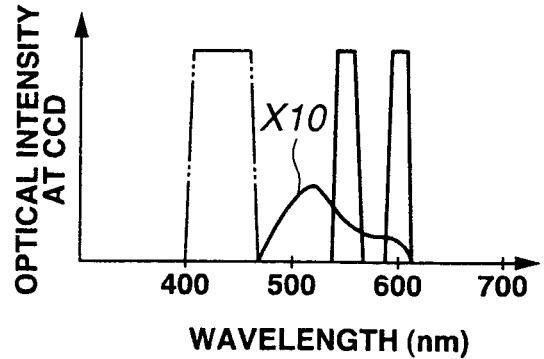
FIG. 17B is a graph showing the characteristic with respect to wavelength of the optical intensity detected photoelectrically by a CCD when skin is observed in the fluorescence observation mode of a filter that is provided, instead of an excitation light cut-off filter, to remove excitation light in the vicinity of 400 nm.

Consequently, if the control circuit 37 performs selection such that the above filter is arranged on the optical path of the endoscope device 1A, when skin is observed in the fluorescent mode, the CCD 28 has a characteristic as shown in FIG. 17B. In this case, the endoscope device 1A can further reduce the self-fluorescence component due to porphyrin. Porphyrin is a substance in which four pyrrole rings are united by methine linkages, a heme is obtained by coupling this porphyrin with iron, and hemoglobin is obtained by further coupling the hem with globin protein.

It should be noted that although in this embodiment the present invention is applied to an image processing device 4A in which the image processing circuit 38 is constructed using a look-up table 51, the present invention is not restricted to this and the present invention could be applied to an image processing device in which the image processing circuit 38 is constructed using a matrix circuit or hue conversion.

Also, although, in this embodiment, the image processing device 4A is constituted so as to adjust the gain of the three input image signals using an image processing circuit 38, the present invention is not restricted to this and the image processing device could be constituted so as to adjust the gain of the three input image signals by for example a preamplifier 32 or automatic gain control (AGC) circuit 33 or D/A conversion circuit 39 or the like.

It should be noted that embodiments constituted by for example combining in partial fashion the various embodiments described above also fall within the scope of the present invention.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An image processing device for fluorescence observation comprising:
    a changeover filter located in an optical path of a light beam generated by a light source device and impinging on body tissue, said light beam including a spectra from an infrared wavelength band to a visible light band, said changeover filter alters said light beam into illumination light or excitation light;
    an image synthesizing section that generates a synthesized image by synthesizing an image signal of a reflected light image sensed by an image pickup element and obtained by illuminating body tissue with said illumination light and an image signal of a fluorescent image sensed by said image pickup element and obtained by illuminating said body tissue with said excitation light, wherein said body tissue is sequentially and non-concurrently illuminated by said illumination light and said excitation light; and
    a gain adjustment section that adjusts a gain of said image signal of said reflected light image and/or said image signal of said fluorescent image such that a boundary of hues of normal tissue and diseased tissue found using optical characteristics of said normal tissue and said diseased tissue is included in a predetermined range with respect to a prescribed standard chromaticity diagram, depending on whether said body tissue that is represented in said synthesized image generated by said image synthesizing section is normal tissue or diseased tissue.

2. The image processing device for fluorescence observation according to claim 1, wherein the image signal of the reflected light image comprises an image signal of a first reflected light image obtained by illuminating body tissue with illumination light of a wavelength band including the optical absorption band of hemoglobin and an image signal of a second reflected light image obtained by illuminating the body tissue with illumination light of a wavelength band including the optical non-absorption band of hemoglobin;
    the image synthesizing section synthesizes the image signal of the first reflected light image, the image signal of the second reflected light image and the image signal of the fluorescent image; and
    the gain adjustment section adjusts at least one gain of the image signal of the first reflected light image, the image signal of the second reflected light image and the image signal of the fluorescent image.

3. The image processing device for fluorescence observation according to claim 2, wherein the image synthesizing section synthesizes the image signal of the first reflected light image, the image signal of the second reflected light image and the image signal of the fluorescent image as respectively different hues.

4. The image processing device for fluorescence observation according to claim 1, wherein
    the image signal of the reflected light image comprises an image signal of a first reflected light image obtained by illuminating body tissue with illumination light of a wavelength band including the optical absorption band of hemoglobin and an image signal of a second reflected light image obtained by illuminating body tissue with illumination light of a wavelength band including the optical non-absorption band of hemoglobin;
    the image synthesizing section performs synthesis with the first reflected light image allocated to a red color, the second reflected light image allocated to a blue color and the fluorescent image allocated to a green color; and
    the gain adjustment section adjusts the gain of the three image signals such that the boundary of the hues of the normal tissue and diseased tissue represented in the synthesized image is included in a range defined by the four points (0.21, 0.53), (0.18, 0.50), (0.23, 0.44) and (0.25, 0.49) with respect to the CIE 1976 UCS chromaticity diagram.

5. The image processing device for fluorescence observation according to claim 1, wherein
the image signal of the reflected light image comprises an image signal of a first reflected light image obtained by illuminating body tissue with illumination light of a wavelength band including the optical absorption band of hemoglobin and an image signal of a second reflected light image obtained by illuminating body tissue with illumination light of a wavelength band including the optical non-absorption band of hemoglobin;
the image synthesizing section performs synthesis with the first reflected light image allocated to a blue color, the second reflected light image allocated to a red color and the fluorescent image allocated to a green color; and
the gain adjustment section adjusts the gain of the thee image signals such that the boundary of the hues of the normal tissue and diseased tissue represented in the synthesized image is included in a range defined by the four points (0.21, 0.53), (0.18, 0.50), (0.23, 0.44) and (0.25, 0.49) with respect to the CIE 1976 UCS chromaticity diagram.

6. The image processing device for fluorescence observation according to claim 1, wherein the boundary of the hues is the point of intersection in the respective probability distribution functions obtained based on the average color tone of pixels in regions of interest that are set in regard to body tissue and diseased tissue, respectively.

7. The image processing device for fluorescence observation according to claim 4, having a normal image mode for generating an image signal of a normal image obtained by successively illuminating body tissue with light of red, green and blue color produced from white light.

8. The image processing device for fluorescence observation according to claim 5, having a normal image mode for generating an image signal of a normal image obtained by successively illuminating body tissue with light of red, green and blue color produced from white light.

9. The image processing device for fluorescence observation according to claim 2, wherein the illumination light of the wavelength band including the optical absorption band of hemoglobin includes 550 nm wavelength.

10. The image processing device for fluorescence observation according to claim 2, wherein the illumination light of the wavelength band including the optical non-absorption band of hemoglobin includes 610 nm wavelength.

11. An image processing device for fluorescence observation comprising:
a changeover filter located in an optical path of a light beam generated by a light source device and impinging on body tissue, said light beam including a spectra from an infrared wavelength band to a visible light band, said changeover filter alters said light beam into illumination light or excitation light;
image synthesizing means that generates a synthesized image by synthesizing an image signal of a reflected light image sensed by an image pickup element and obtained by illuminating body tissue with said illumination light and an image signal of a fluorescent image sensed by said image pickup element and obtained by illuminating said body tissue with said excitation light, wherein said body tissue is sequentially and non-concurrently illuminated by said illumination light and said excitation light; and
gain adjustment means that adjusts a gain of said image signal of said reflected light image and/or said image signal of said fluorescent image such that a boundary of hues of normal tissue and diseased tissue found using optical characteristics of said normal tissue and said diseased tissue is included in a predetermined range with respect to a prescribed standard chromaticity diagram, depending on whether said body tissue that is represented in said synthesized image generated by said image synthesizing section is normal tissue or diseased tissue.

12. The image processing device for fluorescence observation according to claim 11, wherein
the image signal of the reflected light image comprises an image signal of a first reflected light image obtained by illuminating body tissue with illumination light of a wavelength band including the optical absorption band of hemoglobin and an image signal of a second reflected light image obtained by illuminating the body tissue with illumination light of a wavelength band including the optical non-absorption band of hemoglobin;
the image synthesizing means synthesizes the image signal of the first reflected light image, the image signal of the second reflected light image and the image signal of the fluorescent image; and
the gain adjustment means adjusts at least one gain of the image signal of the first reflected light image, the image signal of the second reflected light image and the image signal of the fluorescent image.

13. The image processing device for fluorescence observation according to claim 11, wherein
the image signal of the reflected light image comprises an image signal of a first reflected light image obtained by illuminating body tissue with illumination light of a wavelength band including the optical absorption band of hemoglobin and an image signal of a second reflected light image obtained by illuminating body tissue with illumination light of a wavelength band including the optical non-absorption band of hemoglobin;
the image synthesizing means performs synthesis with the first reflected light image allocated to a red color, the second reflected light image allocated to a blue color and the fluorescent image allocated to a green color; and
the gain adjustment means adjusts the gain of the three image signals such that the boundary of the hues of the normal tissue and diseased tissue represented in the synthesized image is included in a range defined by the four points (0.21, 0.53), (0.18, 0.50), (0.23, 0.44) and (0.25, 0.49) with respect to the CIE 1976 UCS chromaticity diagram.

14. The image processing device for fluorescence observation according to claim 11, wherein
the image signal of the reflected light image comprises an image signal of a first reflected light image obtained by illuminating body tissue with illumination light of a wavelength band including the optical absorption band of hemoglobin and an image signal of a second reflected light image obtained by illuminating body tissue with illumination light of a wavelength band including the optical non-absorption band of hemoglobin,
the image synthesizing means performs synthesis with the first reflected light image allocated to a blue color, the second reflected light image allocated to a red color and the fluorescent image allocated to a green color, and the gain adjustment means adjusts the gain of the three image signals such that the boundary of the hues of the normal tissue and diseased tissue represented in the synthesized image is included in a range defined by the four points (0.21, 0,53), (0.18, 0.50), (0.23, 0.44) and (0.25, 0.49) with respect to the CIE 1976 UCS chromaticity diagram.

15. An image processing device for fluorescence observation comprising:

a light source device that emits a light beam comprising illumination light including two different wavelength bands, a wavelength band including an optical absorption band of hemoglobin and another wavelength band including an optical non-absorption band of hemoglobin, and excitation light in yet another wavelength band for exciting fluorescence;

a changeover filter located in an optical oath of said light beam, wherein said changeover filter alters said light beam into illumination light or excitation light;

an image pickup section that comprises an image pickup element that picks up respectively two reflected light images produced by reflected light obtained by reflection after illuminating body tissue with said illumination light of said two different wavelength bands from said light source device and a fluorescent image produced by fluorescence excited by illuminating body tissue with said excitation light from said light source device wherein said body tissue is sequentially and non-concurrently illuminated by said illumination light and said excitation light; and an image processing section that generates a processed image by signal processing of image signals of said two reflected light images obtained by said image pickup section and an image signal of said fluorescent image;

wherein said image processing section comprises:

a signal input section that inputs thee image signals consisting of said image signals of said two reflected light images picked up by said image pickup section and said image signal of said fluorescent image;

an image synthesizing section that generates a synthesized image by image synthesis of said image signals of said two reflected light images and said fluorescent image signal, wherein one of said image signals of said two reflected light images is an image signal of said wavelength band including said optical absorption band of hemoglobin, and wherein the other of said image signals of said two reflected light images is an image signal of said wavelength band including said optical non-absorption band of hemoglobin; and a gain adjustment section that adjusts a gain of at least one of said image signals of said two reflected light images and said fluorescent image signal that are input by said signal input section such that a boundary of hues of normal tissue and diseased tissue represented in said synthesized image synthesized by said image synthesis section is included in a range defined by the four points (0.21, 0.53), (0.18, 0.50), (0.23, 0.44) and (0.25, 0,49) with respect to the CUB 1976 UCS chromatic city diagram.

16. The image processing device for fluorescence observation according to claim 15, wherein the image synthesizing section effects synthesis by allocating one of the two reflected light images to a red color, allocating the other to a blue color and allocating the fluorescent image to a green color.

17. The image processing device for fluorescence observation according to claim 15, wherein the image synthesizing section effects synthesis by allocating one of the two reflected light images to a blue color, allocating the other to a red color and allocating the fluorescent, image to a green color.

18. The image processing device for fluorescence observation according to claim 15, wherein the boundary of the hues is the point of intersection in the respective probability distribution functions obtained based on the average color tone of pixels in regions of interest that are set in regard to body tissue and diseased tissue, respectively.

19. An image processing device for fluorescence observation comprising:

a light source device that emits a light beam comprising illumination light including two different wavelength bands, a wavelength band including an optical absorption band of hemoglobin and another wavelength band including an optical non-absorption band of hemoglobin, and excitation light in yet another wavelength band for exciting fluorescence;

a changeover filter located in an optical path of said light beam, wherein said changeover filter alters said light beam into illumination light or excitation light;

an image pickup section comprises an image pickup that element that picks up respectively two reflected light images produced by reflected light obtained by reflection after illuminating body tissue with illumination light of said two different wavelength bands from said light source device and a fluorescent image produced by fluorescence excited by illuminating said body tissue with said excitation light from said light source device, wherein said body tissue is sequentially and non-concurrently illuminated by said illumination light and said excitation light; and an image processing section that generates a processed image by signal processing of image signals of said two reflected light images obtained by said image pickup section and an image signal of said fluorescent image;

wherein said image processing section comprises:

signal input means that inputs three image signals consisting of said image signals of said two reflected light images picked up by said image pickup section and said image signal of said fluorescent image;

image synthesizing means that generates a synthesized image by image synthesis of said image signals of said two reflected light images and said fluorescent image signal, wherein one of said image signals of said two reflected light images is an image signal of said wavelength band including said optical absorption band of hemoglobin, and wherein the other of said image signals of said two reflected light images is an image signal of said wavelength band including said optical non-absorption band of hemoglobin; and gain adjustment means that adjusts a gain of said three image signals that are input by the signal input means such that a boundary of hues of normal tissue and diseased tissue represented in said synthesized image synthesized by said image synthesis section is included in a range defined by the four points (0.21, 0.53), (0.18, 0.50), (0.23, 0.44) and (0.25, 0.49) with respect to the CIE 1976 UCS chromaticity diagram.

20. The image processing device for fluorescence observation according to claim 19, wherein the image synthesizing section effects synthesis by allocating one of the two reflected light images to a red color, allocating the other to a blue color and allocating the fluorescent image to a green color.

21. The image processing device for fluorescence observation according to claim 19, wherein the image synthesizing section effects synthesis by allocating one of the two reflected light images to a blue color, allocating the other to a red color and allocating the fluorescent image to a green color.

22. The image processing device for fluorescence observation according to claim 19, wherein the fluorescence wavelength band is a wavelength band including 520 nm wavelength and the two reflected light bands are wavelength bands comprising respectively 550 nm wavelength and 600 nm wavelength.

23. The image processing device for fluorescence observation according to claim 22, wherein the wavelength width of the two reflected light bands is no more than 20 nm.

24. The image processing device of claim 1, wherein said image pickup element sequentially produces said reflected light image and said fluorescent image.

25. The image processing device of claim 1, wherein said illumination light has a wavelength band containing at least a portion of 470 nm to 700 nm.

26. The image processing device of claim 1, wherein said changeover filter sequentially provides said illumination light and said excitation light.

27. The image processing device of claim 1, wherein said image pickup element is selected from the group consisting of one charge coupled element, one charge modulation device, one C-MOS image pickup element, one amplified MOS imager, and one back-illuminated charge coupled device.

28. The image processing device of claim 19, wherein said image pickup element sequentially produces said two reflected light images and said fluorescent image.

29. The image processing device of claim 19, wherein said illumination light including said two different wavelength bands has a wavelength band containing at least a portion of 470 nm to 700 nm.

30. The image processing device of claim 19, wherein said changeover filter sequentially provides said illumination light of the two different wavelength bands and said excitation light.

31. The image processing device of claim 19, wherein said image pickup element is selected from the group consisting of one charge coupled element, one charge modulation device, one C-MOS image pickup element, one amplified MOS imager, and one back-illuminated charge coupled device.

32. The image processing device of claim 1, wherein said changeover filter comprises a nominal illumination filter for transmitting said illumination light and a fluorescent illumination filter for transmitting said excitation light that are concentric and have different radial distances from a center of said changeover filter, and wherein said image processing device further comprises a moving mechanism for moving said changeover filter to select a portion of said changeover filter to be placed in said optical path of said light beam between said nominal illumination filter and said fluorescent illumination filter.

33. The image processing device of claim 11, wherein said changeover filter comprises a nominal illumination filter for transmitting said illumination light and a fluorescent illumination filter for transmitting said excitation light that are concentric and have different radial distances from a center of said changeover filter, and wherein said image processing device further comprises a moving mechanism for moving said changeover filter to select a portion of said changeover filter to be placed in said optical path of said light beam between said nominal illumination filter and said fluorescent illumination filter.

34. The image processing device of claim 15, wherein said changeover filter comprises a nominal illumination filter for transmitting said illumination light and a fluorescent illumination filter for transmitting said excitation light that are concentric and have different radial distances from a center of said changeover filter, and wherein said image processing device further comprises a moving mechanism for moving said changeover filter to select a portion of said changeover filter to be placed in said optical path of said light beam between said nominal illumination filter and said fluorescent illumination filter.

35. The image processing device of claim 19, wherein said changeover filter comprises a nominal illumination fitter for transmitting said illumination light and a fluorescent illumination filter for transmitting said excitation light that are concentric and have different radial distances from a center of said changeover filter, and wherein said image processing device further comprises a moving mechanism for moving said changeover filter to select a portion of said changeover filter to be placed in said optical path of said light beam between said nominal illumination filter and said fluorescent illumination filter.

* * * * *

UNITED STATES PATENT AND TRADEMARK OFFICE
CERTIFICATE OF CORRECTION

PATENT NO.         : 7,324,674 B2                                    Page 1 of 1
APPLICATION NO.    : 10/601496
DATED              : January 29, 2008
INVENTOR(S)        : Takeshi Ozawa et al.

It is certified that error appears in the above-identified patent and that said Letters Patent is hereby corrected as shown below:

<u>Column 21, Claim 15, Line 26:</u>

"illuminating body" should read -- illuminating said body --

<u>Column 21, Claim 15, Line 36:</u>

"inputs thee image" should read -- inputs three image --

<u>Column 21, Claim 15, Line 58:</u>

"CUB" should read -- CIE --

<u>Column 22, Claim 19, Line 23:</u>

"an image pickup section comprises an image pickup that"

should read

--an image pickup section that comprises an image pickup--

Signed and Sealed this

Seventeenth Day of June, 2008

JON W. DUDAS
*Director of the United States Patent and Trademark Office*